(12) United States Patent
Finch et al.

(10) Patent No.: US 10,738,342 B2
(45) Date of Patent: Aug. 11, 2020

(54) SYSTEM FOR MICROBIAL SPECIES DETECTION, QUANTIFICATION AND ANTIBIOTIC SUSCEPTIBILITY IDENTIFICATION

(71) Applicant: Urinary Technologies, Inc., Lake Elmo, MN (US)

(72) Inventors: Michael D. Finch, Minneapolis, MN (US); Kee Onn Fong, Minneapolis, MN (US); Saurabh Kotian, Tempe, AZ (US); Cyrus B. Munshi, Blaine, MN (US); Advitiya Mahajan, Falcon Heights, MN (US); Beth A. Lindborg, Saint Paul, MN (US)

(73) Assignee: Urinary Technologies, Inc., Lake Elmo, MN (US)

( * ) Notice: Subject to any disclaimer, the term of this patent is extended or adjusted under 35 U.S.C. 154(b) by 0 days.

(21) Appl. No.: 16/551,702

(22) Filed: Aug. 26, 2019

(65) Prior Publication Data
US 2020/0071740 A1 Mar. 5, 2020

Related U.S. Application Data

(60) Provisional application No. 62/725,026, filed on Aug. 30, 2018.

(51) Int. Cl.
*C12Q 1/04* (2006.01)
*B01L 3/00* (2006.01)
(Continued)

(52) U.S. Cl.
CPC .......... *C12Q 1/04* (2013.01); *B01L 3/502753* (2013.01); *B01L 3/502776* (2013.01);
(Continued)

(58) Field of Classification Search
CPC .................................................... B01L 3/5027
See application file for complete search history.

(56) References Cited

U.S. PATENT DOCUMENTS

| 5,821,066 A | 10/1998 | Pyle et al. |
| 7,048,890 B2 | 5/2006 | Coehoorn et al. |

(Continued)

FOREIGN PATENT DOCUMENTS

WO 2006066216 A3 6/2006

OTHER PUBLICATIONS

Altobelli et al., "Integrated Biosensor Assay for Rapid Uropathogen Identification and Phenotypic Antimicrobial Susceptibility Testing", European urology focus, 2017, vol. 3, No. 2-3, pp. 293-299, HHS Public Access Author Manuscript Version internal p. 1-13.

(Continued)

*Primary Examiner* — William H. Beisner
(74) *Attorney, Agent, or Firm* — Charles L. Dennis, II

(57) ABSTRACT

Several microfluidic chips are used to significantly accelerate the time to identify and quantify microbes in a biological sample and test them for antibiotic resistance, particularly for urinary tract infections. A first microfluidic chip uses antibody or similar probes to identify and quantify any microbes present. The same or a similar chip uses antibody or similar probes to identify microbes with DNA or RNA known to indicate antibiotic resistance. Another microfluidic chip tests for antibiotic susceptibility of any microbes by growing them in very small wells in the presence of antibiotics, reducing the time required for such testing by as much as 95%. Another microfluidic chip runs traditional urinalysis or similar tests.

20 Claims, 4 Drawing Sheets

Specification includes a Sequence Listing.

(51) Int. Cl.
| | |
|---|---|
| G01N 33/569 | (2006.01) |
| G01N 35/10 | (2006.01) |
| C12Q 1/02 | (2006.01) |
| G01N 35/00 | (2006.01) |

(52) U.S. Cl.
CPC ....... *C12Q 1/025* (2013.01); *G01N 33/56905* (2013.01); *G01N 33/56911* (2013.01); *G01N 35/1004* (2013.01); *B01L 3/5027* (2013.01); *B01L 2200/027* (2013.01); *B01L 2200/0647* (2013.01); *B01L 2200/16* (2013.01); *B01L 2300/047* (2013.01); *B01L 2300/0877* (2013.01); *G01N 2035/00237* (2013.01)

(56) References Cited

U.S. PATENT DOCUMENTS

| | | | |
|---|---|---|---|
| 7,399,585 | B2 | 7/2008 | Gau |
| 7,727,206 | B2 | 6/2010 | Gorres |
| 8,333,499 | B2 | 12/2012 | Gau et al. |
| 8,557,050 | B1 | 10/2013 | Gay et al. |
| 9,535,032 | B2 | 1/2017 | Gau |
| 9,632,085 | B2 | 4/2017 | Super et al. |
| 2007/0287147 | A1* | 12/2007 | Nagamune ............... C12Q 1/04 435/5 |
| 2010/0075298 | A1 | 3/2010 | Creek et al. |
| 2010/0254914 | A1 | 10/2010 | Park et al. |
| 2016/0032350 | A1 | 2/2016 | Hou et al. |
| 2016/0215324 | A1 | 7/2016 | Srinivasan et al. |
| 2017/0146515 | A1 | 5/2017 | Ingber et al. |
| 2017/0298456 | A1 | 10/2017 | Holder et al. |

OTHER PUBLICATIONS

Avesar et al., "Rapid phenotypic antimicrobial susceptibility testing using nanoliter arrays", Proceedings of the National Academy of Sciences, Jun. 26, 2017, vol. 114, pp. E5787-E5795.
Agarwal J. et al., "Pathogenomics of uropathogenic *Escherichia coli*", Indian Journal of Medical Microbiology, 30(2):141-149 (2012).
Ahmed A. et al., "Biosensors for Whole-Cell Bacterial Detection", Clinical Microbiology Reviews, 27(3):631-646 (Jul. 2014).
Arshad M. et al., "Urinary Tract Infections in the Infant", Clinical Perinatology, 42(1):17-28 (Dec. 24, 2014).
Avesar J. et al., "Rapid phenotypic antimicrobial susceptibility testing using nanoliter arrays", Proceedings of the National Academy of Sciences USA, 114(23):E5787-E5795 (Jun. 26, 2017).
Baltekin Ö. et al., "Antibiotic susceptibility testing in less than 30 min using direct single-cell imaging", Proceedings of the National Academy of Sciences USA, 114(34):9170-9175 (Aug. 22, 2017).
Barczak A.K. et al., "RNA signatures allow rapid identification of pathogens and antibiotic susceptibilities", Proceedings of the National Academy of Sciences of the United States of America, 109(16):6217-6222 (Apr. 17, 2012).
Choi J et al., "Rapid antibiotic susceptibility testing by tracking single cell growth in a microfluidic agarose channel system", Lab on a Chip, 13:280-287 (2013).
Chu C.M. et al., "Diagnosis and treatment of urinary tract infections across age groups", American Journal of Obstetrics and Gynecology Expert Reviews, 219(1):40-51 (Jul. 2018).
Fleckenstein J.M. et al., "Novel Antigens for enterotoxigenic *Escherichia coli* (ETEC) Vaccines", NIH Public Access Author Manuscript, Expert Review of Vaccines, published in final form as 13(5):631-639 (2014).
Flores-Mireles A.L. et al., "Urinary tract infections: epidemiology, mechanisms of infection and treatment options", Nature Reviews | Microbiology, 13:269-284 (May 2015).
Foxman B., "Epidemiology of urinary tract infections: incidence morbidity and economic costs", American Journal of Medicine 113(1):5-13 (2002).
Hodkinson B.P. et al., "Next-Generation Sequencing: A Review of Technologies and Wound Microbiome Research", Advances in Wound Care, 4(1):50-58 (2015).
Ilyas M., "Next-Generation Sequencing in Diagnostic Pathology", Pathobiology, DOI: 10.1159/000480089:1-14 (Oct. 31, 2017).
Kurata T et al., "Novel Essential Gene Involved in 16S rRNA Processing in *Escherichia coli*", Journal of Molecular Biology, 427:955-965 (2014).
Li Y et al., "Nanomagnetic Competition Assay for Low-Abundance Protein Biomarker Quantification in Unprocessed Human Sera", Journal of the American Chemical Society, 132:4388-4392 (Mar. 1, 2010).
Lin C. et al., "Urine analysis in microfluidic devices", Analyst, 136:2669-2688 (2011).
Masajtis-Zagajewska A. et al., "New markers of urinary tract infection", Clinica Chimica Acta, 471:286-291 (2017).
Mohan R et al., "A multiplexed microfluidic platform for rapid antibiotic susceptibility testing", Biosensors and Bioelectronics, 49:118-125 (May 9, 2013).
Nayak S. et al., "Microfluidics-based point-of-care test for serodiagnosis of Lyme Disease", www.nature.com/scientificreports, 6:35069 | DOI: 10.1038/srep35069 (Oct. 11, 2016).
Pankhurst L.J. et al., "Rapid, comprehensive, and affordable mycobacterial diagnosis with whole-genome sequencing: a prospective study", Lancet Respiratory Medicine 2016(4):49-58 (Dec. 3, 2015).
Pereira F. et al., "Identification of species by multiplex analysis of variable-length sequences", Nucleic Acids Research, 38(22):1-17 (Oct. 4, 2010).
Raub C.B. et al., "Sequestration of bacteria from whole blood by optimized microfluidic cross-flow filtration for Rapid Antimicrobial Susceptibility Testing", Sensors and Actuators B: Chemical, 210:120-123 (Oct. 25, 2014).
Savory N et al., "Selection of DNA aptamers against uropathogenic *Escherichia coli* NSM59 by quantitative PCR controlled Cell-SELEX", Journal of Microbiological Methods, 104:94-100 (Jul. 4, 2014).
Shcappert S.M. et al., "Ambulatory medical care utilization estimates for 2007", Vital and Health Statistics, Series 13, Data from the National Health Survey, Apr. 1, 2011(169):1-38.
Srinivasan R et al., "Use of 16S rRNA Gene for Identification of a Broad Range of Clinically Relevant Bacterial Pathogens", PLOS ONE, 10(2): e0117617 (Feb. 6, 2015).
Tsang H. et al., "NastyBugs: A simple method for extraction antimicrobial resistance information from metagenomes", F1000 Reearch 2017, 6:1971:1-9 (Nov. 8, 2017).
Wang W. et al., "Surface Modification for Protein and DNA Immobilization onto GMR Biosensor", IEEE Transactions on Magnetics, 49(1):296-299 (Jan. 2013).
Warren A.D. et al., "Point-of-care diagnostics for noncommunicable diseases using synthetic biomarkers and paper microfluidics", Proceedings of the National Academy of Sciences of the United States of America, 111(10):3671-3676 (Mar. 11, 2014).
Xu B. et al., "Simultaneous Identification and Antimicrobial Susceptibility Testing of Multiple Uropathogens on a Microfluidic Chip with Paper-Supported Cell Culture Arrays", Analytical Chemistry, 2016(88):11593-11600 (Nov. 9, 2016).
Yang Y. et al., "Separating and Detecting *Escherichia coli* in a Microfluidic Channel for Urinary Tract Infection Applications", Journal of Microelectromechanical Systems, 20(4):819-827 (Aug. 2011).
Yarza P. et al., "Uniting the classification of cultured and uncultured Bacteria and Archaea using 16S rRNA gene sequences", Nature Reviews Microbiology, 12:635-645 (Aug. 2014).

* cited by examiner

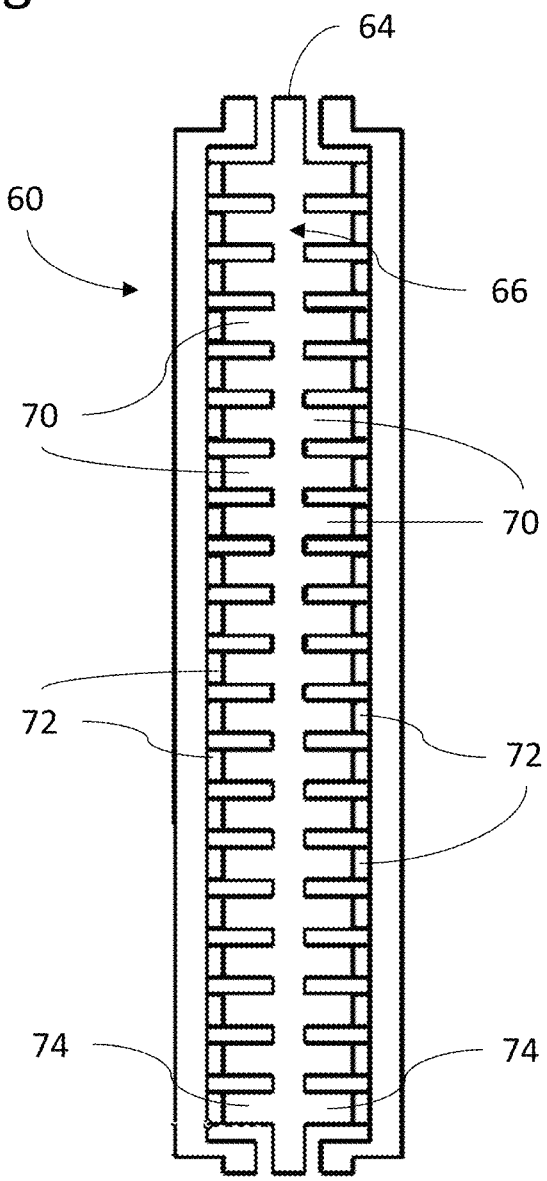

SYSTEM FOR MICROBIAL SPECIES DETECTION, QUANTIFICATION AND ANTIBIOTIC SUSCEPTIBILITY IDENTIFICATION

CROSS-REFERENCE TO PROVISIONAL APPLICATION

This application claims priority to U.S. Provisional Patent Application Ser. No. 62/725,026, filed on 30 Aug. 2018, titled "System for Microbial Species Detection, Quantification and Antibiotic Susceptibility Identification".

TECHNICAL FIELD

The present invention relates to a system for detecting and quantifying one or more species of microbe present in a biological sample and identifying antibiotic susceptibility of such microbes. More specifically, the invention relates to a system for detecting, quantifying and identifying microbes as well as antibiotic susceptibility of the microbes in urine samples from patients with possible urinary tract infections.

BACKGROUND

Urinary tract infections (UTIs) are microbial infections which pose a significant public health threat. In 2007, there were 10.5 million outpatient UTI visits for medical care in the United States, and 21.3% of those visits were to emergency. UTIs are also prevalent worldwide, especially in countries with large populations and public sanitation challenges.

The United States Center for Disease Control and Prevention describes UTIs as infections that occur when a microbe enters the urinary tract. UTIs can arise from poor hygiene, intercourse, abnormal anatomy, and the presence of bacteria, virus or fungus. Some populations are at a higher risk of getting UTIs—women and girls have higher rates of UTIs than men due to anatomical structure. The elderly and patients with urinary incontinence or catheter implants are also at higher risk for UTIs. UTI symptoms are painful and have been described by patients as causing feelings of pain or burning while urinating, frequent urination and the feeling of a need to urinate despite having an empty bladder. Other common symptoms include low fever (about 38° C.), cloudy or bloody urine and pressure or cramping in the groin or lower abdomen. Further complicating accurate and timely diagnosis, UTI symptoms often present differently based on patient age. Infants with UTIs often present with a fever, fussy disposition, or reduced appetite. In contrast, elderly UTI patients may be asymptomatic or may exhibit symptoms resembling dementia, accompanied by excessive fatigue and incontinence. Despite the range of presentation, accurate and timely diagnosis is critical, as untreated UTIs can develop into more severe conditions such as kidney infections or sepsis.

In current practice, the diagnosis of UTIs involves clinical and physical exams, followed by both a sterile urinalysis and a positive urine culture test that usually takes multiple days to complete and often is not used in outpatient settings. Foxman B., "*Epidemiology of urinary tract infections: incidence, morbidity, and economic costs*", American Journal of Medicine 113(1):5-13 (2002). This 'gold standard' procedure is followed for patients from whom a mid-stream urine sample can be collected. For patients who cannot urinate on their own, urine may be collected via a catheter, which is at the least uncomfortable and can be painful.

The urinalysis can be done relatively quickly and can tell providers whether an infection may be present in the urinary tract due to reading elevated levels of white blood cells in the sample, but it cannot identify the microbe causing the infection, quantify the level of infection or indicate the appropriate antibiotic.

The urine culture test detects the specific pathogens present, quantifies the microbial load, and can identify potential antibiotic resistance, but it takes substantial time. In this test, a urine sample is swabbed onto growth medium in a Petri plate. After a suitable incubation period to enable microbial replication, the Petri plate is visually inspected for microbes, which are then identified and quantified by a trained specialist. If looking for antibiotic resistance, multiple test plates may be made, with each subjected to a different antibiotic to test for resistance to that antibiotic. This approach has the advantage that it can find any type of microbe and look for any type of antibiotic resistance, but the disadvantage that the microbes must reproduce long enough to produce colonies visibly differentiable by the human eye. It takes a minimum of 18 hours, and often up to 72 hours, to obtain results from a urine culture test. Notably, when a urine culture test is run to diagnose a suspected UTI, as much as 80% of the time the test results are negative—that is, the test indicates that the patient does not have a UTI.

The lengthy time required for current urine culture tests results in very unsatisfactory treatment approaches. In most circumstances, and especially in pediatric or geriatric cases, clinicians tend to default-prescribe broad-spectrum antibiotics that cover a range of the microbes most commonly associated with UTIs, long before the urine culture test results are available. Since as much as 80% of the urine culture test results show no infection, this means that 80% of the patients are being prescribed antibiotics when they are of no value whatsoever. If subsequent urine culture test results indicate that the patient has a microbial infection, but not one susceptible to the antibiotic used initially, the original antibiotic will be discontinued and the correct antibiotic prescribed. This assumes the clinician can actually reach the patient at that point, which often is not the case.

In both the situation when the patient had no UTI, and the one when the patient has an infection that is not susceptible to the initial antibiotic, the patient is prescribed an ineffective antibiotic. This is not helpful for the patient and promotes the growth of antibiotic-resistant microbes.

In summary, UTIs are extremely common, but the current diagnosis and treatment processes are widely perceived as flawed by practitioners. In particular, the slow detection and quantification of the microbial load in a given infection by a urine culture test means that antibiotics are often prescribed to patients who do not actually have a UTI, and even in patients who do have a UTI, the initially prescribed antibiotics may target the wrong microbe or the microbe may be resistant to that antibiotic, requiring a post-test change in antibiotics. This extremely common issue contributes to antibiotic resistance, which increasingly threatens public health.

To improve treatment, a novel method of microbe detection, quantification and identification of antibiotic resistance is needed that works in hours instead of days, and that finds the correct treatment for at least the microbes known to frequently cause such infections, all at a reasonably low cost due to the high volume of tests required.

BRIEF SUMMARY

The present invention is based on the recognition that the current gold standard urine culture test is excessive. Specifically, the current test assumes that there is no advance knowledge of what microbes may be causing a UTI, so it is necessary to look for all possible microbes. But that assumption is very far from reality. Instead, nearly all UTIs are caused by a surprisingly limited number of microbes.

For example, in the United States, just one microbial family causes 75% of all uncomplicated UTIs, and 9 microbial families cause nearly all uncomplicated UTIs. Specifically, in uncomplicated UTIs, uropathogenic *Escherichia coli* (UPEC) causes 75% of all uncomplicated UTIs, *Klebsiella pneumoniae* causes 6%, *Staphylococcus saprophyticus* (6%), *Enteroccus* spp. (5%), group B *Streptococcus* (GB S) (3%), *Proteus mirabilis* (2%), *Pseudomonas aeruginosa* (1%), *Staphylococcus aureus* (1%) and *Candida* spp (1%). For complicated UTIs, the frequencies per microbe are slightly different, but just 4 microbial families cause over 90% of all complicated UTIs, and the same microbial families causing uncomplicated UTIs cause nearly all complicated UTIs. Specifically, UPEC causes 65% of all complicated UTIs, *Klebsiella pneumoniae* causes 8%, *Enteroccus* spp. (11%), GBS (2%), *Proteus mirabilis* (2%), *Pseudomonas aeruginosa* (2%), *Staphylococcus aureus* (3%) and *Candida* spp (7%). Ana L. Fores-Mireles et al., "*Urinary tract infections: epidemiology, mechanisms of infection and treatment options*", Nature Reviews Microbiology 13: 269-284 (2015). Similarly, in the United Kingdom, depending on how and where UTIs were acquired, the same species cause at least 85% of all UTIs. D. J. Farrell et al., "*A UK Multicentre Study of the Antimicrobial Susceptibility of Microbial Pathogens Causing Urinary Tract Infection*", Journal of Infection 46:94-100 (2003).

This enables a completely different approach to diagnosing UTIs. Instead of looking for any microbe which might possibly be present, the present invention uses probes to look for the specific microbes which are known to cause nearly all UTIs. The present invention uses DNA, RNA, antibody, aptamer or small molecule probes specifically targeting these common microbes to detect and quantify the microbes much more quickly, without the need to conduct a urine culture test. This new test should take less than hour, which is fast enough for a patient to wait for test results. For the 80% of tests which are negative, this would enable the clinician to move on to other possible causes of the patient's symptoms and avoid prescribing a completely unnecessary antibiotic. For the 20% of tests which are positive, by diagnosing which microbe is causing the UTI, the test will enable the physician to have a better idea of what antibiotics to prescribe to treat the specific microbe.

According to a further aspect of the invention, the present invention uses DNA, RNA, antibody, aptamer or small molecule probes specifically targeting the presence of nucleotides or proteins that are known to provide antibiotic resistance, enabling rapid identification of which antibiotics will not work against the microbes that are present. Like the identification and quantification test, this test should take less than hour, which is fast enough for a patient to wait for test results. This ensures that they will be sent home with a prescription for the correct antibiotic, if an antibiotic is appropriate.

A further aspect of the present invention provides a backup diagnostic antibiotic resistance identification test using an approach more similar to a traditional urine culture test, but in a new system which enables it to be done much faster. This new test is based on the recognition of two problems with the traditional test:

First, the traditional test requires microbes to replicate enough times to be visible by a human. The time required for such replication is what causes the test to take 18-72 hours. In a system according to the present invention, small wells are used instead of Petri plates and a sensor is used to detect the microbes. The sensor can detect the microbes after far fewer reproduction cycles than the human eye can, shortening the incubation time to at most a few hours.

Second, the traditional test requires a highly trained person to read the test. This is expensive and can take considerable time, especially if there are multiple varieties of microbes and/or if tests are run to identify antibiotic resistance, requiring multiple Petri plates. In a system according the present invention, software analyzes the sensor output for each well in at most a few seconds, shortening the time required to read the test to at most a few minutes, even when many cells are used.

More specifically according to this aspect of the invention, a system identifies antibiotic resistance using a chip with a plurality of wells. Each well has growth medium, antibiotics and a reporter indicating the presence of live microbes. Once provided with a urine sample, the wells are sealed and incubated. A sensor then is used to detect activity from the reporter, which in turn indicates microbe growth in the different wells. But the wells can be much smaller than a Petri dish—less than 1 cc, and preferably less than 0.1 cc—allowing the incubation process to take dramatically less time, since less replication is needed. This test should take 1-7 hours, and with very small wells 1-3 hours. A patient may not want to wait for the test result, but a prescription for the correct antibiotic could be sent to the pharmacy in a few hours, and the patient could be instructed to pick it up then.

Given that any system providing the tests above will necessarily be handling and testing urine, it also would be convenient if the same system could conduct a conventional urinalysis, which today is done separately from the urine culture test. Test results from a urinalysis typically are ready in less than 1 hour.

To these ends, the present invention provides a system for conducting urinalysis, detecting and quantifying the presence of the common species of microbes which cause UTIs, identifying any antibiotic resistance as shown by DNA or RNA or the presence of other macromolecules known to provide such, and testing a range of antibiotics for efficacy against any microbes which are present, whether or not they have such DNA or RNA known to provide antibiotic resistance.

To conduct these tests, the system has a fixed hardware portion with replaceable microfluidic test chips. The hardware receives a urine sample and delivers it to each of the chips. Various reactants on the chip then conduct the relevant tests. The hardware than measures the results of the tests on the chips, and reports the results, either directly to a screen on the system, or to an associated computer system, or both.

Preferably, the system uses three chips.

The first chip is a microbial detection chip (or MDC) with multiple sections, preferably 2-100, more preferably 4-50, more preferably 8-25. Each section is provided with a volume for capturing microbes from a urine sample and for testing them with a probe. Each such probe can test for a specific microbe or for the presence of a specific strand of DNA or RNA indicating antibiotic resistance. In use, the system delivers urine to the different sections, which then identify and quantify the presence of the relevant microbes and/or the relevant DNA or RNA strands. The system them reads the results from each section, preferably optically.

One notable difference between the MDC and the urine culture test commonly used today is that this system tests for the presence of the specific microbial families known to cause nearly all UTIs v looking for any and all types of microbes which may be present. Similarly, the MDC can test for the specific microbial features known to provide antibiotic resistance. And all of this can be done in a short time, likely under 1 hour.

The second chip is an antibiotic susceptibility chip (or ASC) with multiple wells, preferably at least 2, more preferably at least 12, more preferably at least 20. In use, the system delivers into each well urine mixed with growth medium and a reporter, such as resazurin, which will report the presence and amount of living microbes. Alternatively, the growth medium and reporter can be preloaded into each well and just urine added. The wells are then each isolated and incubated to enable any microbes reproduce. Preferably, at least one well contains no antibiotics, as a control. The other sections each are pre-loaded with different antibiotics, to test for resistance to each antibiotic. Alternatively, the antibiotics can be mixed with the urine sample prior to delivery. After a suitable incubation period for growth of any microbes, the system checks and reports on the level of microbes present in each well. Either directly or by comparison to the control well, the results will indicate which antibiotics would be the most effective at controlling any microbial infection.

The ASC functions as a backup to the MDC. The ASC is agnostic to specific types of microbes—it tests for antibiotic resistance in any microbes that may be present. It does this directly by testing which antibiotics do and do not have an effect, and how much of an effect. The size of the wells can be much smaller than a Petri dish—less than 1 ml and preferably less than 0.1 ml. This dramatically reduced size enables the test to run much faster than a conventional urine culture test, e.g., 1-7 hours, and likely 1-3 hours in small wells. In addition, little skill is required to run or read the test—the urine sample is provided and the test runs automatically.

The third chip is a urinalysis chip (UC). The UC includes reactants similar to those used today on dip sticks for urinalysis. These reactants change color depending on the amount of a particular chemical in the urine. The system then optically reads the color to determine the test results. This test would take essentially the same amount of time as the current dipsticks, which is a minute or two.

The chips can each be separate, or they can all be on a replaceable cartridge. Preferably, all portions of the system which contact the urine sample are also part of an easily replaceable cartridge. Alternatively, the system would include provisions for flushing, cleaning and sterilizing any part of the system which contacts the urine sample.

The system enables identification and quantification of microbes and antibiotic resistance via known DNA or RNA in about one hour, broad-spectrum antibiotic susceptibility testing can be completed in at most a few hours and conventional urinalysis can be completed in a few minutes. The initial time period of about an hour 1 for completion of urinalysis, identification and quantification of microbes and known antibiotic resistance is short enough that it is reasonable for a patient to wait for the test results. This enables the clinician to quickly move on to testing for other hypotheses if the test is negative and the patient does not have a UTI, which is especially useful for patient groups with a high frequency of negative results. The few hour time period for the agnostic antibiotic susceptibility test means the clinician can tell the patient to go to the pharmacy 4 hours after completion of the initial tests to pick up an antibiotic prescription, and it will be an antibiotic that will actually work. This simultaneously will improve patient care and dramatically reduce the prescription of ineffective antibiotics.

The above summary is not intended to describe each embodiment or every implementation of the invention. Other embodiments, features and advantages of the invention will be apparent from the following detailed description thereof, from the drawings and from the claims.

BRIEF DESCRIPTION OF THE DRAWINGS

FIG. 4 is an antibiotic susceptibility chip (or ASC) for use in the system of FIG. 1.

DETAILED DESCRIPTION

Figure 1:
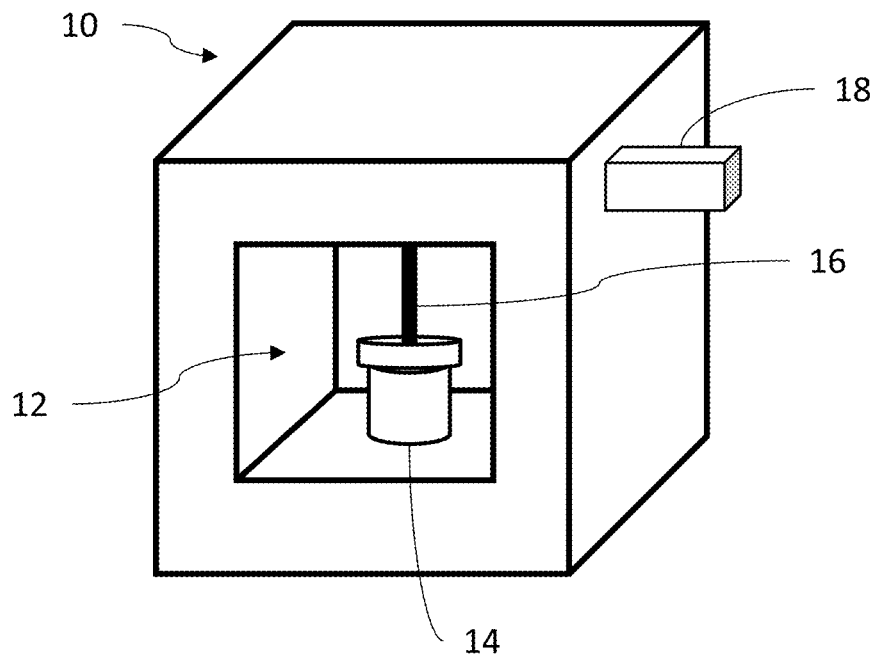
FIG. 1 is projection view of an embodiment of a system according to the present invention.

As shown in FIG. 1, a first embodiment according to the present invention includes a system 10 having therein a sample receiving area 12. A urine sample vial 14 containing urine received from a patient can be placed in the sample receiving area 12. The system 10 further includes a sample withdrawal pipette 16 which can be inserted into the urine sample vial 20 to withdraw urine therefrom. The system 10 also includes a cartridge 18 replaceably insertable into the apparatus 10, which contains microfluidic chips to be further described below.

Figure 2:
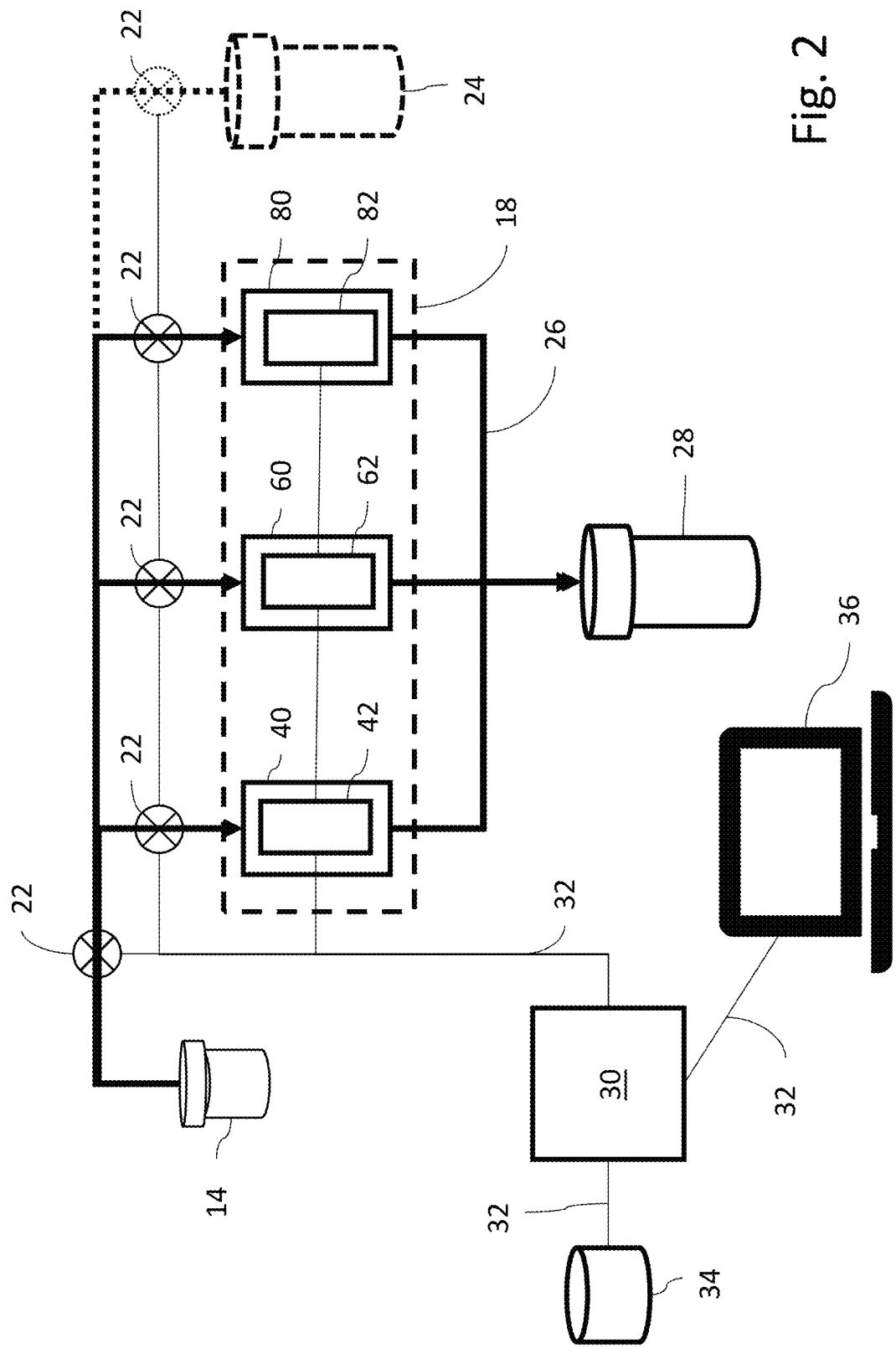
FIG. 2 is block diagram of the system of FIG. 1.

Referring now to FIG. 2, cartridge 18 contains three microfluidic chips, a microbe detection chip (MDC) 40, an antibiotic susceptibility chip (ASC) 60 and a urinalysis chip (UC) 80. The sample withdrawal pipette 16 is connected via sample distribution lines 20 to provide urine samples to each of the microfluidic chips 40, 60, 80. Flow of sample from the vial 14 to the chips 40, 60, 80 is controlled by a series of pumps 22. If desired, various other fluids, such as buffer or cleansing solution can be provided in one or more additional vials 24, which also are connected to the chips 40, 60, 80 via distribution lines 20 and controlled by pumps 22. Liquid flowing out of the chips 40, 60, 80 is collected via waste collection lines 26 and delivered to a waste collection vial 28. Three sensors are provided in the systems 10, an MDC sensor 42 for MDC 40, an ASC MDC sensor 62 for ASC 60 and a UC MDC sensor 82 for UC 80. In each case, the relevant MDC sensor 42, 62, 82 is positioned to make measurements of the associated chip 40, 60, 80. A programmed CPU 30 is connected via electrical lines 32 to control operation of the pumps 22 and to operate and collect data from the sensors 42, 62, 82. The CPU 30 also is connected via electrical lines 32 to mass storage 34 and one or more I/O devices 36, which may be a screen on the system 10 or an independent laptop, mobile device, centralized medical record system or the like. Operation of the system will be described further below in connection with each chip 40, 60, 80. The chips 40, 60, 80 preferably are all in replaceable cartridge 18, so they may easily be replaced after each use.

MDC Structure and Operation

Figure 3:
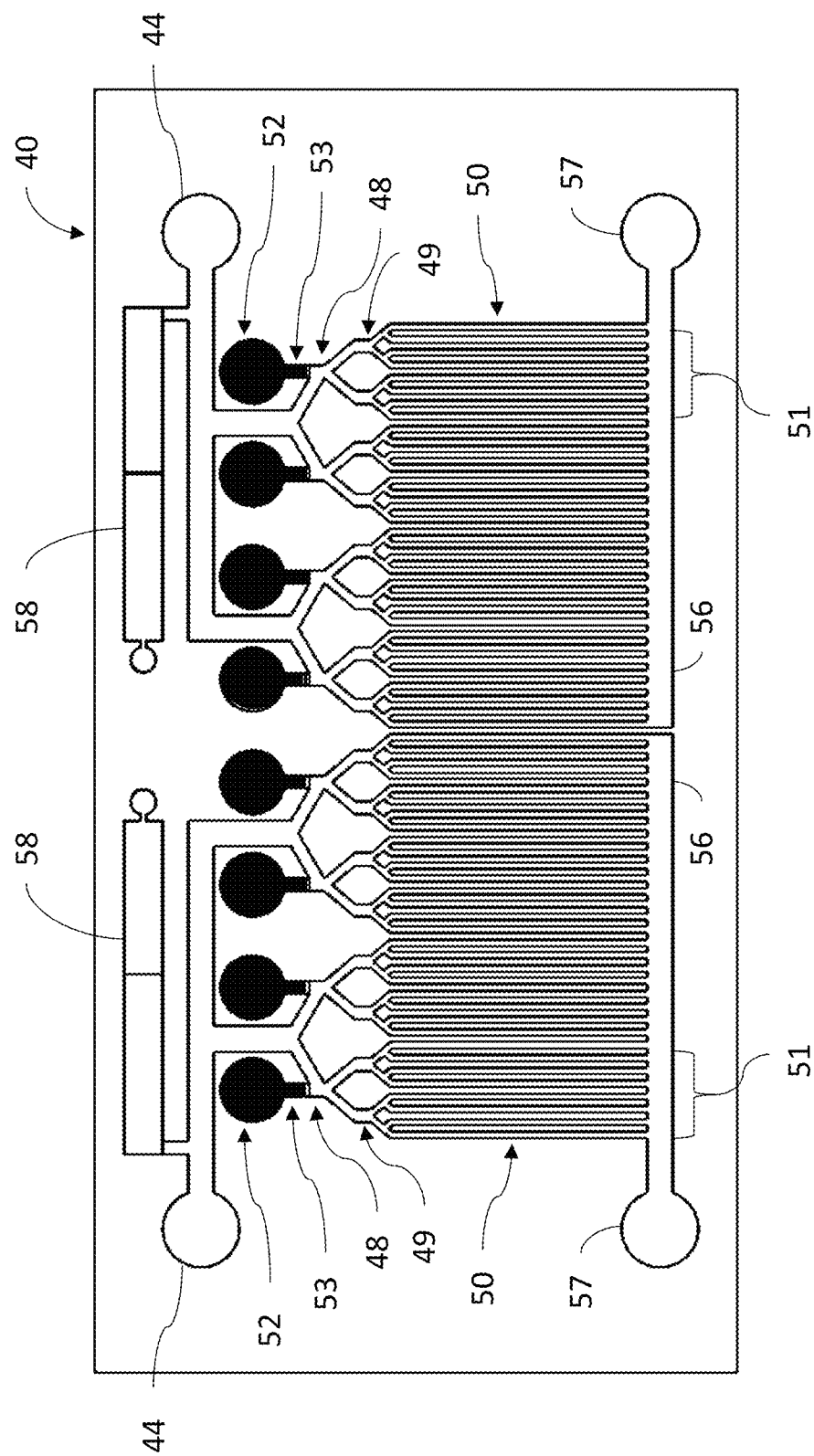
FIG. 3 is a microbe detection chip (or MDC) for use in the system of FIG. 1.

MDC 40 is shown in greater detail in FIG. 3. Inlets 44 are provided on the chip 40 to receive the urine sample from sample distribution line 20. The urine sample then is distributed via distribution channels 46 and branch structures 48 to a series of microfluidic channels 50. Each microfluidic channel 50 is coated with materials to which microbes will adhere, such as, but not limited to antibodies, proteins, double-stranded DNA, single-stranded DNA, double-stranded RNA, single-stranded RN and aptamers, any of which may comprise 100% natural amino acids, a mix of natural and un-natural amino acids, or 100% un-natural amino acids. The coatings may attach to all forms of microbes, or may target a specific species or family, matching the relevant probes discussed further below.

A series of probe reservoirs 52 each contain a probe for a different microbe, which will be described in more detail below, and which is held in place in the probe reservoir by a sealant plug 53. Each probe reservoir 52 is connected into the branch structure 48 at a sub-branch level 49 such that it will connect to a specific cluster 51 of microfluidic channels 50. When each probe is released from its probe reservoir 52 as described below, it will flow into its associated cluster 51 and not into the other clusters. At the other end of each microfluidic channel 50 is a collection channel 56 connect to outlets 57, through which fluids flowing through the MDC 40 can be removed from the MDC 40. Optionally, fluid reservoir 58 may also be provided on the MDC 40, which can contain a variety of fluids for use in the MDC 40, such as, but not limited to, buffering, lysing agent or the like. Such fluids can thereby be provided from the reservoirs 60 on the chip, or from the external solution vial 24, as most convenient for the design of a particular embodiment of the system 10.

As will be apparent from an inspection of FIG. 3, two sets of channels 50 are shown, each with four corresponding reservoirs 52. The number of sets, the number of reservoirs and the number of channels in each set can be expanded or reduced, as needed for the design of a particular embodiment of the system 10.

In use, urine is provided to the inlets 44, which will then flow through the distribution channels 46, branches 46, microfluidic channels 50 and collection channels 56 to the outlets 57. As the urine passes through the microfluidic channels 50, it will adhere to the walls due to the coatings. Urine input then is halted and the channels 50 are flushed with a lysing solution, either from an on-chip reservoir 58 or the external solution vial 24. As the lysing solution flows through the microfluidic channels 50, it will lyse all microbes present on the walls of the channels. The lysing solution is halted, and a buffer solution then is provided either from an on-chip reservoir 58 or an external solution vial 24. As this buffer solution flows through the microfluidic channels 50, it will flush out the lysing solution and any other materials not bound to the channel walls.

Preferably, the material of the sealant plugs 53 closing the probe reservoirs 52 is selected such that the buffer solution will dissolve the sealant plugs 53. If not, then a separate solution can be run through the MDC 40 to dissolve the sealant plugs 53.

When the sealant plugs 53 dissolve, the probes will then flow out of each probe reservoir 52 into the associated cluster 51 of microfluidic channels 50. The probes will bind to the aspects of each microbe in each channel for which they probe, if present. After an appropriate time period for the probes to bind, a washing solution may be flushed through the system to wash away any unbound materials, leaving only bound probes. The presence and number of bound probes is measured using the MDC sensor 42, and the resultant data is provided to the CPU 30, which stores it in the mass storage 32.

The MDC structure as described above is best used in situations where the probes need target intracellular material, e.g., DNA. If the probes target only proteins or other compounds expressed on the surface of the microbes, then the structure and method can be simplified. Specifically, according to this embodiment of the invention, probe reservoirs 52 can be omitted, and the probes are used as the coating on the insides of the channel sets. The lysing step described above can be skipped, since the probes will adhere to the surface of the microbes and lysing is unnecessary.

MDC Probes

The probes used in the MDC generally take the form of an attacher-reporter complex, that is, they have an attacher part which is configured to attach to a specific microbe or portion of a microbe, and a reporter part bound to the attacher part which is readily detectable by an external device. Creating such attacher-reporter probes is a well known process to one of ordinary skill in the art, who is aware of many approaches to achieve this end.

Among the most common attachers is a single-stranded or double-stranded DNA or RNA sequence which will bind to a genus-specific, species-specific or subspecies-specific DNA, RNA, oligonucleotide, peptide or similar sequences from a microbe. For example, such attachers can target attached DNA Sequences Nos. 1 and/or 2 to identify *Escherichia coli*, Sequences Nos. 3, 4, 5 and/or 6 to identify *Klebsiella pneumoniae*, Sequences Nos. 7 and/or 8 to identify *Staphylococcus saprophyticus*, Sequences Nos. 9 and/or 10 to identify *Enterococcus* spp., Sequences Nos. 11 and/or 12 to identify *Proteus mirabilis*, Sequences Nos. 13 and/or 14 to identify *Pseudomonas aeruginosa*, Sequences Nos. 15 and/or 16 to identify *Staphylococcus aureus*, Sequences Nos. 17 and/or 18 to identify *Candida* spp., Sequences Nos. 19 and/or 20 to identify *Candida albicans*, Sequences Nos. 21 and/or 22 to identify *Chlamydia trachomatis*, and Sequences Nos. 23 and/or 24 to identify *Mycoplasma genitalium*. Similarly, attached Sequences Nos. 25 and/or 26 can be used to identify microbes which carry indicia of resistance to the penicillin group of antibiotics, Sequences Nos. 27 and/or 28 to ciproflaxin, Sequences Nos. 29 and/or 30 to levofloxacin, and Sequences Nos. 31 and/or 32 to cephalexin.

Another well known approach to designing attachers is to fabricate aptamers, which are specific oligonucleotide or peptide molecules that bind to a specific target molecule. Aptamers can be engineered to bind to a known surface marker that is present on a specific microbial species, hence achieving the objective of attaching to only one species of microbe. Aptamers can also be designed to target the virulence factors present on any and all bacterial species and subspecies.

Suitable aptamers can be designed to target specific proteins that are present on the surface of the organism (such as outer membrane proteins (OMPs), virulence factors, IgGs, etc.) or the proteins and target sequences (such as DNA, mRNA, tRNA, sRNA) inside the cells of the organisms. An example of a surface marker that the antibodies and/or aptamers could bind to is the O Antigen present on the microbial surface. An example of a target sequence is the 16S ribosomal RNA sequence highly abundant in bacterial species. The 16S sequence has been identified for many species. For example, Sequence No. 1 is the 16S sequence for *Escherichia coli*.

While such DNA, RNA and aptamer attachers are the most common, many other forms of attachers are well known and can be used in system 10 according to the present invention. For example, and without limitation, such attachers could be natural or synthetic DNA, RNA, antibodies, aptamers or other amino acid structures, using natural and/or non-naturally occurring amino acids, which recognize microbial surface molecules, microbial intracellular proteins, and/or microbial DNA or RNA. All such compounds may be truncated (such as Fab, Fab'2, scFv), engineered for multivalency or otherwise to detect more than one target. All such attachers may also be engineered to resist enzymatic or non-enzymatic degradation.

Any of these attachers can suitably be selected or designed to target species and subspecies including, but not limited to: *Acetobacter aurantius, Acinetobacter baumannii, Actinomyces israelii, Agrobacterium radiobacter, Agrobacterium tumefaciens, Anaplasma phagocytophilum, Azorhizobium caulinodans, Aztobacter vinelandii, Bacillus anthracis, Bacillus brevis, Bacillus cereus, Bacillus fusiformis, Bacillus licheniformis, Bacillus megaterium, Bacillus mycoides, Bacillus stearothermophilus, Bacillus subtilis, Bacillus thuringiensis, Bacteroides fragilis, Bacteroides gingivalis, Bacteroides melaninogenicus, Bartonella henselae, Bartonella quintana, Bordetella bronchiseptica, Bordetella pertussis, Borrelia burgdorferia, Brucella, Brucella abortus, Brucella melitensis, Brucella suis, Burkholderia mallei, Burkholderia pseudomallei, Burkholderia cepacia, Calymmatobacterium granulomatis, Campylobacter coli, Campylobacter fetus, Campylobacter jejuni, Campylobacter pylori, Chlamydia trachomatis, Chlamydophila pneumoniae, Chlamydophila psittaci, Clostridium botulinum, Clostridium difficile, Clostridium perfringens, Clostridium tetani, Corynebacterium diphtheriae, Corynebacteriym fusiforme, Coxiella burnetti, Ehrlichia chaffeensis, Enterobacter cloacae, Enterococcus avium, Enterococcus durans, Enterococcus faecalis, Enteroccous faecium, Enterococcus galllinarum, Enterococcus maloratus, Eschericichia coli, Francisella tularenisis, Fusobacterium nucleatum, Gardnerella vaginalis, Haemophilus ducreyi, Haemophilus influenzae, Haemophilus parainfluenzae, Haemophilus pertussis, Hamephilus vaginalis, Helicobacter pylori, Klebsilla pneumoniae, Lactobacillus acidophilus, Lactobacillus bulgaricus, Lactobacillus casei, Lactococcus lactis, Legionella pneumophila, Listeria monocytogenes, Methanobacterium extroquens, Microbacterium multiforme, Micrococcus luteus, Moraxella catarrhalis, Mycobacterium avium, Mycobacterium bovis, Mycobacterium diphtheriae, Mycobacterium intracellulare, Mycobacterium leprae, Mycobacterium lepraemurium, Mycobacterium phlei, Mycobacterium smegmatis, Mycobacterium tuberculosis, Mycoplasma fermentans, Mycoplasma genitalium, Mycoplasma hominis, Mycoplasma penetrans, Mycoplasma pneumoniae, Neisseria gonorrhoeae, Neisseria meningitidis, Pasteurella multocida, Pasteurella tularensis, Peptostreptococcus, Porphyromonas gingivalis, Prevotella melaninogenica, Pseudomonas aeruginosa, Rhizobium radiobacter, Rickettsia prowazekii, Rickettsia psittaci, Rickettsia quintana, Rickettsia rickettsii, Rickettsia trachomas, Rochalimaea henselae, Rochalimaea quintana, Rothia dentocariosa, Salmonella enteritidis, Salmonella typhi, Salmonella typhimurium, Serratia marcescens, Staphylococcus aureus, Staphylococcus epidermidis, Stenotrophomonas maltophillia, Streptococcus agalactiae, Streptococcus avium, Streptococcus bovis, Streptococcus cricetus, Streptococcus faecium, Streptococcus faecalis, Streptococcus ferus, Streptococcus gallinarum, Streptococcus lactis, Streptococcus mitior, Streptococcus mutans, Streptococcus oralis, Streptococcus pneumoniae, Streptococcus pyogenes, Streptococcus rattus, Streptococcus salivarius, Streptococcus sanguis, Streptococcus sobrinus, Treponema pallidum, Treponema denticola, Vibrio cholerae, Vibrio comma, Vibrio parahaemolyticus, Vibrio vulnificus, Viridans streptococci, Wolbachia, Yersinia enterocolitica, Yersinia pestis,* and *Yersinia pseudotuberculosis.*

The most commonly used reporters are fluorescent molecules, which either naturally emit light when bound or are stimulated to fluoresce. Examples include but are not limited to naturally occurring fluorescein, synthetic Texas red dye, fluoro-max red and green dye, fluorescent carboxylate-modified particles with europium chelators, fluorescent streptavidin coated particles with europium chelators, and dry fluorescent particles.

Alternatives reporters include:

a. Chemiluminescent molecules and visible spectrum luminescence detected via means of visible-spectrum microscopy and imaging.

b. Radioactive nuclides detected via means of radioactive emissions of alpha and beta particles.

c. Giant magnetoresistance-based magnetic nanoparticles detected using an applied magnetic field and/or detected using an electrical signal via means of attachment to a GMR-sensitive surface coating.

d. Magnetic nanoparticles (MNPs) including but not limited to: iron oxide MNP, iron nickel MNP, iron cobalt MNP and other MNP materials based on iron, nickel, cobalt and other ferromagnetic elements or compounds. Such magnetic nanoparticles sometimes are coated with an organic and/or inorganic material such as streptavidin, oleic acid, oleylamine, polyethylene glycol, polysaccharide, polyhydroxybutyrate, biopolymers, iron oxide and like.

e. Surface plasmon structures which fluoresce or otherwise are readily detectable.

The attachers and reporters may be joined together by any suitable means, such as ligation, conjugation or via an intermediary structure, such as a bead or iron oxide nanoworm.

The attachers, reporters and/or attacher reporter complex may also be ligated with a peptide, conjugated to a protein, or otherwise modified for enhanced stability, such as by PEGylation.

As a specific example, the MDC 40 can be provided with 32 probe reservoirs 52. Each probe reservoir contains a probe formed by a fluorescent reporter and an antibody attacher selected to attach to one of the attached Sequences Nos. 1-32. Each MDC sensor 42 is a fluorescent sensor. The luminescent reporter preferably is the same for each probe, so that a single MDC sensor 42 can be used and moved from one channel 50 to the next. Alternatively, an MDC sensor 42 can be aligned with each channel 50. Results from the probes targeting sequences 1-24 will indicate the presence of the related species. Results from the probes targeting sequences 25-32 will indicate antibiotics which would be ineffective.

Note that using all of the Sequences Nos. 1-32 as described results in redundancy, since at least two sequences have been provided for each target. While it is not always necessary to have such redundancy, doing so will enhance the accuracy of the test.

ASC Structure and Operation

The ASC 60 is shown in greater detail in FIG. 4. An inlet 64 at one end of the chip connects via main channel 66 to the outlet 68 at the opposite end. A plurality of wells 70 are provided along the length of and connected to the main channel 66. Each of the wells 70 is pre-loaded with a different antimicrobial or antibiotic 72, except that one or more wells 74 may be left empty of antimicrobials and antibiotics to serve as a control. Preferably, the wells 70, 74 also are pre-loaded with a growth medium and a reporter compound, such as, but not limited to, resazurin, which will fluoresce in the presence of living microbes.

Examples of possible antimicrobials and antibiotics 72 to be used include, without limitation, amikacin, aminoglycosides, amoxycillin, amoxycillin-clavulanate, aztreonam, β-lactams, carbapenems, carbenicillin, ceffriaxone, cefixime, cefoperazone, cefotaxime, cefpodoxime, cefprozil, ceftazidime, cefuroxime, coamoxiclav, cephalexin, cephalosporins, chloramphenicols, ciprofloxacin, clindamycin, colistin, cotrimoxazole, doxycycline, erythromycin, flucloxacillin, fluoroquinolones, folic acid inhibitors, foloxacin, fusidic acids, gentamicin, glycopeptides, kanamycin, lipopeptides, lyncosamides, macrolides, meropenem, metronidazoles, monobactams, moxifloxacin, mupirocin, nalidixic acid, neomycin, nitrofurantoins, norfloxacin, ofloxacin, oxazolidinones, penicillin, piperacillin-tazobactam, pivmecillinam, polymyxin b, quinolones, rifampicin, streptogramins, sulfamethoxazole, sulfonamides, tetracyclines, trimethoprim, vancomycin.

In use, if the wells 70, 74 are not pre-loaded with growth medium and a reporting compound, urine is mixed with growth medium and a reporting compound. Urine or the urine/growth medium/reporting compound mixture is supplied into inlet 64, flows down the main channel 66, into the wells 70, 74, with any excess exiting through outlet 68. Once the wells 70, 74 are filled, a high viscosity oil, such as, but not limited to, FC-40, is supplied into inlet 64. Due to its viscosity, the oil will flow down the main channel 66, but will not meaningfully enter the wells 70, 74, thus forming an oil plug which effectively seals each of the wells 70, 74 from the other wells 70, 74. The ASC 60 then is incubated for an appropriate time period to allow microbial replication.

Following incubation, the ASC sensor 62 will measure the amount of microbe in each well by detecting the reporter compound, provide the resultant data to the CPU 30, which then stores the data in mass storage 34. The CPU 30 then can evaluate the level of efficacy of each antimicrobial or antibiotic 72 against microbes in the urine sample either directly by determining lack of any microbe in a well 70 or indirectly by comparing growth rates between cells with antimicrobials or antibiotics 70 and the control well 74. The CPU 30 stores the analytic results in the mass storage 34. By providing levels of efficacy for each antibiotic, the lowest cost, narrowest spectrum antibiotic can be selected which will still be effective.

To minimize time for completion of the test, the wells 70, 74 should be made as small as is consistent with distinguishing efficacy of the relevant antibiotics, for example, <1 ml, and preferably <0.1 ml. This will minimize the amount of microbial replication required before the measurements can be taken.

While the ASC 60 shown in FIG. 4 has 40 wells 70, 74, it will be understood that the number of wells 70, 74 can be increased or decreased depending on the number of antimicrobials or antibiotics to be tested, and the level of redundancy desired in the design of a specific embodiment of the system 10.

As a specific example, the ASC 60 has 44 wells 70, 74. Two control wells 74 are provided, and two wells 70 each are pre-loaded with amikacin, amoxicillin-clavulanate, ampicillin, cefotaxime, cefixime, ceftriaxone, cephalexin, cefpodoxime, ciprofloxacin, cefprozil, coamoxiclav, fosfomycin, gentamicin, levofloxacin, nitrofurantoin, norfloxacin, ofloxacin, pivmecillinam, sulfamethoxazole, and trimethoprim. The reporter compound is resazurin and the ASC sensor 72 is a fluorescence sensor. Preferably, a single ASC sensor 72 can be moved to measure each well 70, 74. Alternatively, an ASC sensor 72 can be aligned with each well 70, 74. Results from the test will indicate which of the antibiotics are most and least effective against the microbes which are present.

Two wells 70, 74 for the control and each antibiotic may be used to provide redundancy. It is not necessary to have such redundancy but doing so should increase accuracy of the test.

UC Structure and Operation

Figure 5:
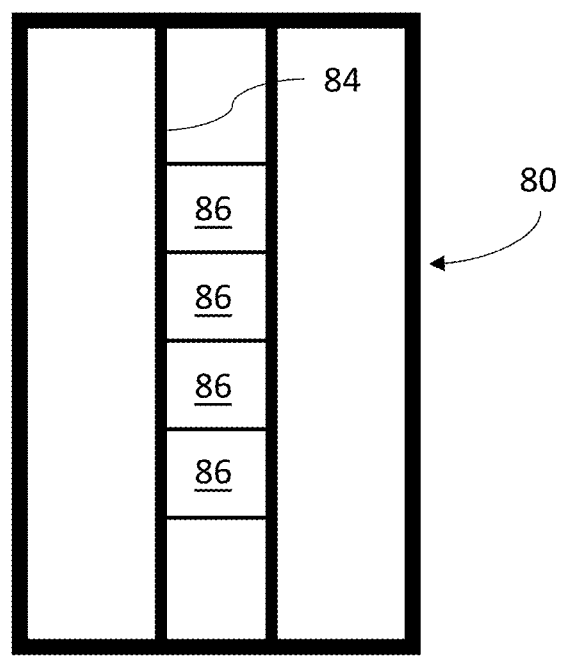
FIG. 5 is urinalysis chip (or UC) for use in the system of FIG. 1.

UC 80 is shown in greater detail in FIG. 5. UC 80 includes a channel 84 extending from the top to the bottom of the chip as shown in the drawing, with UC measurement sections 86 provided to sense various compounds in the urine. Preferably, these sections match the measurements typically used for urinalysis, e.g., sections to measure leukocytes, nitrites, urobilinogen, proteins, pH, hemoglobin, specific gravity, ketones, bilirubin and glucose. To achieve this, each section is pre-coated with the same materials as are used on commercially available dipsticks to make the measurements with current products today, such as those provided by Siemens Multistix®, Roche Chemstrip®, McKesson Consult® and Boehringer Combur-Test® urine test strips. These dipsticks typically test parameters such as leukocytes, nitrites, urobilinogen, proteins, pH, hemoglobin, specific gravity, ketones, bilirubin and glucose via colorimetric measurement.

In use, urine is supplied at one end of channel 84, flows through the channel 84 and out the other end. The relevant colorimetric chemicals in sections 86 will then react with the urine, changing color to indicate the measurements. If desired, a buffer or similar solution may be provided from solution vial 21 to flow through channel 84 to remove any remaining urine. In this configuration, the UC sensor 82 is a colorimeter and is positioned to be able to read the colors of the various sections 86. When the measurement is complete, UC sensor 82 provides the data to the CPU 30, which stores it in the mass storage 34.

Once the various tests are completed, the CPU 30 generates and provides at least one report to the I/O device 36. Preferably, the CPU 30 generates at least two reports: The first one is generated after completion of the urinalysis and microbial detection by the MDC 40 and UC 80, since they do not require incubation and can be run quickly. The second report is generated after completion of the antibiotic susceptibility test by the ASC 60, which takes longer due to the required incubation period.

As will be apparent to one of skill in the art, the system has been described with reference to urine samples to test for UTIs but could readily be adapted to use with other biologic samples to test for other problems. For example, blood, sputum, saliva, mucous or even swabs from the cheek or a wound could be used as the initial biological sample for the system. Depending on the sample, it may be necessary to first add sterile water or saline to the sample to make it sufficiently liquid to flow through the system described. In addition, it may be desirable to change the specific detection compounds used for identification and quantification of microbes to match those likely to cause infections at the biologic location being tested, and other characteristics, e.g., blood chemistry, may be tested instead of conducting a urinalysis. Similarly, the specific microbes described and for which sequences have been provided are bacteria, but the same approach can be used to analyze possible viral, fungal, prion and other infections. But it will be seen that the system as a whole is readily adaptable for a wide variety of tests, sometimes just by substituting different chips.

One skilled in the art will appreciate that the present invention can be practiced with embodiments other than those disclosed. The disclosed embodiments are presented for purposes of illustration and not limitation, and the present invention is limited only by the claims that follow.

What is claimed is:

1. An apparatus for analyzing a biological sample, comprising:
   a. a microfluidic microbe detection chip (MDC), the MDC comprising:
      i. a plurality of microfluidic branches, an internal surface of each branch comprising a substance to which microbes will adhere;
      ii. inlets connected to each said microfluidic branch for receiving the biological sample and delivering it to said plurality of microfluidic branches,
      iii. a plurality of probe reservoirs, each said reservoir containing a supply of probes and connected to a subset of said plurality of microfluidic branches to deliver said probe to said subset of microfluidic branches, and
      iv. outlets connected to said plurality of microfluidic branches for removing fluid therefrom;
   b. a sample transfer mechanism for receiving the biological sample and delivering it to said inlets of said MDC;
   c. at least one MDC solution reservoir, each said reservoir containing a solution and connected to said plurality of microfluidic branches to deliver said solution to said plurality of microfluidic branches;
   d. at least one MDC sensor adjacent to said plurality of microfluidic branches to measure the presence of said probes therein;
   e. a programmed control system for operating the apparatus, receiving measurements from said at least one MDC sensor and reporting the measurements.

2. The apparatus of claim 1, wherein the biological sample is selected from the group consisting of urine, blood, sputum, saliva, mucous and swabs from solid tissue.

3. The apparatus of claim 1, wherein each said probe comprises an attacher-reporter complex.

4. The apparatus of claim 3, wherein an attacher portion of each attacher-reporter complex is selected from the group consisting of natural or synthetic DNA, RNA, antibodies, aptamers or other amino acid structures, using natural and/or non-naturally occurring amino acids and which recognize microbial surface molecules, microbial intracellular proteins or microbial DNA or RNA of microbes.

5. The apparatus of claim 4, wherein each said attacher portion attaches to a portion of the microbial surface molecules, microbial intracellular proteins or microbial DNA or RNA which identifies a specific microbe, the microbe being selected from the group consisting of the 1 to 10 microbes most likely to cause an infection in the type of biological sample being tested.

6. The apparatus of claim 5, wherein said microbes targeted by said probes are selected to match the 1 to 10 microbes most likely to cause a urinary tract infection in a specific geography.

7. The apparatus of claim 5, wherein each said probe targets a microbe selected from the group consisting of Acetobacter aurantius, Acinetobacter baumannii, Actinomyces israelii, Agrobacterium radiobacter, Agrobacterium tumefaciens, Anaplasma phagocytophilum, Azorhizobium caulinodans, Aztobacter vinelandii, Bacillus anthracis, Bacillus brevis, Bacillus cereus, Bacillus fusiformis, Bacillus licheniformis, Bacillus megaterium, Bacillus mycoides, Bacillus stearothermophilus, Bacillus subtilis, Bacillus thuringiensis, Bacteroides fragilis, Bacteroides gingivalis, Bacteroides melaninogenicus, Bartonella henselae, Bartonella quintana, Bordetella bronchiseptica, Bordetella pertussis, Borrelia burgdorferia, Brucella, Brucella abortus, Brucella melitensis, Brucella suis, Burkholderia mallei, Burkholderia pseudomallei, Burkholderia cepacia, Calymmatobacterium granulomatis, Campylobacter coli, Campylobacter fetus, Campylobacter jejuni, Campylobacter pylori, Chlamydia trachomatis, Chlamydophila pneumoniae, Chlamydophila psittaci, Clostridium botulinum, Clostridium difficile, Clostridium perfringens, Clostridium tetani, Corynebacterium diphtheriae, Corynebacteriym fusiforme, Coxiella burnetti, Ehrlichia chaffeensis, Enterobacter cloacae, Enterococcus avium, Enterococcus durans, Enterococcus faecalis, Enteroccous faecium, Enterococcus galllinarum, Enterococcus maloratus, Eschericichia coli, Francisella tularenisis, Fusobacterium nucleatum, Gardnerella vaginalis, Haemophilus ducreyi, Haemophilus influenzae, Haemophilus parainfluenzae, Haemophilus pertussis, Hamephilus vaginalis, Helicobacter pylori, Klebsilla pneumoniae, Lactobacillus acidophilus, Lactobacillus bulgaricus, Lactobacillus casei, Lactococcus lactis, Legionella pneumophila, Listeria monocytogenes, Methanobacterium extroquens, Microbacterium multiforme, Micrococcus luteus, Moraxella catarrhalis, Mycobacterium avium, Mycobacterium bovis, Mycobacterium diphtheriae, Mycobacterium intracellulare, Mycobacterium leprae, Mycobacterium lepraemurium, Mycobacterium phlei, Mycobacterium smegmatis, Mycobacterium tuberculosis, Mycoplasma fermentans, Mycoplasma genitalium, Mycoplasma hominis, Mycoplasma penetrans, Mycoplasma pneumoniae, Neisseria gonorrhoeae, Neisseria meningitidis, Pasteurella multocida, Pasteurella tularensis, Peptostreptococcus, Porphyromonas gingivalis, Prevotella melaninogenica, Pseudomonas aeruginosa, Rhizobium radiobacter, Rickettsia prowazekii, Rickettsia psittaci, Rickettsia quintana, Rickettsia rickettsii, Rickettsia trachomae, Rochalimaea henselae, Rochalimaea quintana, Rothia dentocariosa, Salmonella enteritidis, Salmonella typhi, Salmonella typhimurium, Serratia marcescens, Staphylococcus aureus, Staphylococcus epidermidis, Stenotrophomonas maltophillia, Streptococcus agalactiae, Streptococcus avium, Streptococcus bovis, Streptococcus cricetus, Streptococcus faecium, Streptococcus faecalis, Streptococcus ferus, Streptococcus gallinarum, Streptococcus lactis, Streptococcus mitior, Streptococcus mutans, Streptococcus oralis, Streptococcus pneumoniae, Streptococcus pyogenes, Streptococcus rattus, Streptococcus salivarius, Streptococcus sanguis, Streptococcus sobrinus, Treponema pallidum, Treponema denticola, Vibrio cholerae, Vibrio comma, Vibrio parahaemolyticus, Vibrio vulnificus, Viridans streptococci, Wolbachia, Yersinia enterocolitica, Yersinia pestis, and Yersinia pseudotuberculosis.

8. The apparatus of claim 5, wherein each said attacher portion attaches to a portion of the microbial surface molecules, microbial intracellular proteins or microbial DNA or RNA which identifies a specific microbe, the microbe being selected from the group consisting of the 4 to 10 microbes most likely to cause an infection in the type of biological sample being tested.

9. The apparatus of claim 4, wherein said attacher portion attaches to a portion of the DNA or RNA of said microbe which identifies resistance to a specific antibiotic or antimicrobial.

10. The apparatus of claim 9, wherein said resistance identifying DNA or RNA identifies resistance to antibiotics and antimicrobials selected from the group consisting of amikacin, aminoglycosides, amoxycillin, amoxycillin-clavulanate, aztreonam, lactams, carbapenems, carbenicillin, ceftriaxone, cefixime, cefoperazone, cefotaxime, cefpodoxime, cefprozil, ceftazidime, cefuroxime, coamoxiclav, cephalexin, cephalosporins, chloramphenicols, ciprofloxacin, clindamycin, colistin, cotrimoxazole, doxycycline, erythromycin, flucloxacillin, fluoroquinolones, folic acid inhibitors, foloxacin, fusidic acids, gentamicin, glycopeptides, kanamycin, lipopeptides, lyncosamides, macrolides, meropenem, metronidazoles, monobactams, moxifloxacin, mupirocin, nalidixic acid, neomycin, nitrofurantoins, norfloxacin, ofloxacin, oxazolidinones, penicillin, piperacillin-tazobactam, pivmecillinam, polymyxin b, quinolones, rifampicin, streptogramins, sulfamethoxazole, sulfonamides, tetracyclines, trimethoprim, vancomycin.

11. The apparatus of claim 3, wherein a reporter portion each attacher-reporter complex is selected from the group consisting of fluorescent structure, chemiluminescent structure, radioactive nuclides, magnetic nanoparticles, giant magnetoresistance-based magnetic nanoparticles, coated magnetic nanoparticles and surface plasmon structures.

12. The apparatus of claim 1, wherein said programmed control system is programmed to operate the apparatus according to the method comprising:
a. causing said sample transfer mechanism to receive said biological sample and deliver it to said MDC inlets, and thereby to said plurality of microfluidic branches such that at least some of any microbes in said biological sample will adhere to said internal surfaces of said plurality of microfluidic branches and any excess biological sample will exit said plurality of microfluidic channels via said outlets;
b. causing a lysing solution from a first said MDC solution reservoir to be delivered to said plurality of microfluidic branches to lyse microbes adhered therein;
c. causing a buffer solution from a second said MDC solution reservoir to be delivered to said plurality of microfluidic branches to substantially flush out through the outlets both the lysing solution and any microbes not adhered to the said plurality of microfluidic branches;
d. causing each said probe to be delivered to its said connected subset of microfluidic branches to bind to any of the probe's target DNA or RNA adhered inside the microfluidic branches;
e. causing a washing solution from a third said MDC solution reservoir to be delivered to said plurality of microfluidic branches to flush unbound probes out through the outlets;
f. causing the MDC sensor adjacent to each said subset of microfluidic branches to measure the level of probes bound inside the microfluidic branches; and
g. reporting the level of probes bound inside the microfluidic branches.

13. The apparatus of claim 1, wherein said MDC is on a replaceable cartridge.

14. The apparatus of claim 1, further comprising:
a. an antibiotic susceptibility chip (ASC), the ASC comprising:
   i. a main channel;
   ii. a plurality of wells formed adjacent to and connected to said main channel, each said well comprising a volume to receive said biological sample and at least some of said wells pre-coated with at least one antibiotic;
   iii. an inlet near one end of said main channel;
   iv. an outlet near an opposite end of said wells;
b. said sample transfer mechanism further being connected to said ASC inlet in parallel to said MDC inlet;
c. at least one ASC solution reservoir containing a solution and connected to said ASC inlet;
d. a reporter in each said well to report the presence and amount of microbes in said well;
e. at least one ASC sensor adjacent to said ASC wells to measure said reporter; and
f. wherein said programmed control system is further configured to operate said ASC, to receive measurements from said at least one ASC sensor and to report the results.

15. The apparatus of claim 14, wherein said programmed control system is programmed to operate the apparatus according to the method comprising:
a. causing said sample transfer mechanism to receive said biological sample and deliver it to said ASC inlet to substantially fill said ASC main channel and plurality of wells, and with any excess biological sample exiting said ASC main channel via said ASC outlet;
b. causing a high viscosity solution from a first said ASC solution reservoir to be delivered to said ASC main channel to block off each said well from the other said wells;
c. incubating said ASC for a time period and under environmental conditions conducive to microbial growth;
d. causing said at least one ASC sensor adjacent to each said wells to measure the level of microbes in each said well as indicated by said reporter; and
e. reporting the number of microbes found inside each said well.

16. The apparatus of claim 15, wherein said reporter comprises resazurin and wherein said at least one ASC sensor comprises a fluorescent sensor for the detection of resazurin combined with a living microbe.

17. The apparatus of claim 1, further comprising:
a. a microfluidic urinalysis chip (UC), the UC comprising:
   i. a channel having a plurality of UC sensor areas along a length thereof, each UC sensor area having a surface which will bind to or react with a specific constituent of said biological sample;
   ii. an inlet along said channel at one end of said plurality of UC sensor areas;
   iii. an outlet along said channel on an opposite end of said plurality of UC sensor areas;
b. said sample transfer mechanism further being connected to said UC inlet in parallel to said MDC inlets;
c. at least one UC sensor adjacent to each said UC sensor areas to measure a value of said specific constituent of said biological sample in each said UC sensor area; and d. wherein said programmed control system is further configured to operate said UC, to receive measurements from said at least one UC sensor and to report the measurements.

18. The apparatus of claim 17, wherein said plurality of UC sensor areas comprise areas to measure characteristics selected from the group consisting of bilirubin, glucose, hemoglobin, ketones, leukocytes, nitrites, pH, protein, specific gravity, urobilinogen.

19. The apparatus of claim 17, wherein said programmed control system further is programmed to operate the apparatus according to the method comprising:
  a. causing said sample transfer mechanism to receive said biological sample and deliver it to said UC inlet, and thereby to said UC channel and plurality of UC sensor areas with any excess biological sample exiting said UC channel via said UC outlet;
  b. causing said at least one UC sensor adjacent to each said sensor areas to measure the value of constituents bound in the sensor area; and
  c. reporting the value of constituents bound in the sensor areas.

20. An apparatus for diagnosing a urinary tract infection using a urine sample, comprising:
  a. a microfluidic microbe detection chip (MDC), the MDC comprising:
    i. a plurality of microfluidic branches, an internal surface of each branch comprising a substance to which microbes will adhere;
    ii. inlets connected to each said microfluidic branch for receiving the urine sample and delivering it to said plurality of microfluidic branches, a plurality of probe reservoirs, each said reservoir containing a supply of probes and connected to a subset of said plurality of microfluidic branches to deliver said probe to said subset of microfluidic branches, wherein each said probe attaches to a portion of the microbial surface molecules, microbial intracellular proteins or microbial DNA or RNA which identify a specific microbe, the microbes being selected from the group consisting of the 1 to 10 microbes most likely to cause a urinary tract; and
    iii. outlets connected to said plurality of microfluidic branches for removing fluid therefrom;
  b. an antibiotic susceptibility chip (ASC), the ASC comprising:
    i. a main channel;
    ii. a plurality of wells formed adjacent to and connected to said main channel, each said well comprising a volume to receive the urine sample and at least some of said wells pre-coated with at least one antibiotic;
    iii. a reporter in each said well to report the presence and amount of living microbes in said well;
    iv. an inlet near one end of said main channel;
    v. an outlet near an opposite end of said plurality of wells;
  c. a sample transfer mechanism for receiving the urine sample and delivering it to said inlets of said MDC and said ASC;
  d. at least one solution reservoir, each said reservoir containing a solution and connected to said plurality of microfluidic branches or said main channel to deliver said solution to said plurality of microfluidic branches;
  e. at least one MDC sensor adjacent to said plurality of microfluidic branches to measure the presence of said probes therein;
  f. at least one ASC sensor adjacent to said ASC wells to measure said reporter; and
  g. a programmed control system for operating the apparatus to deliver the urine sample and solutions from said reservoirs to said MDC and ASC, receiving measurements from said at least one MDC sensor and said at least one ASC sensor and to report the measurements.

* * * * *

SEQUENCE LISTING

<160> NUMBER OF SEQ ID NOS: 32

<210> SEQ ID NO 1
<211> LENGTH: 770
<212> TYPE: DNA
<213> ORGANISM: Escherichia coli

<400> SEQUENCE: 1

| | | | | | |
|---|---|---|---|---|---|
| aaattgaaga | gtttgatcat | ggctcagatt | gaacgctggc | ggcaggccta | acacatgcaa | 60 |
| gtcgaacggt | aacaggaaga | agcttgctct | ttgctgacga | gtggcggacg | ggtgagtaat | 120 |
| gtctgggaaa | ctgcctgatg | gagggggata | actactggaa | acggtagcta | ataccgcata | 180 |
| acgtcgcaag | accaaagagg | gggaccttcg | ggcctcttgc | catcggatgt | gcccagatgg | 240 |
| gattagctag | taggtggggt | aacggctcac | ctaggcgacg | atccctagct | ggtctgagag | 300 |
| gatgaccagc | cacactggaa | ctgagacacg | gtccagactc | ctacgggagg | cagcagtggg | 360 |
| gaatattgca | caatgggcgc | aagcctgatg | cagccatgcc | gcgtgtatga | agaaggcctt | 420 |
| cgggttgtaa | agtactttca | gcggggagga | agggagtaaa | gttaatacct | ttgctcattg | 480 |
| acgttacccg | cagaagaagc | accggctaac | tccgtgccag | cagccgcggt | aatacggagg | 540 |
| gtgcaagcgt | taatcggaat | tactgggcgt | aaagcgcacg | caggcggttt | gttaagtcag | 600 |
| atgtgaaatc | cccgggctca | acctgggaac | tgcatctgat | actggcaagc | ttgagtctcg | 660 |
| tagaggggg | tagaattcca | ggtgtagcgg | tgaaatgcgt | agagatctgg | aggaataccg | 720 |
| gtggcgaagg | cggccccctg | gacgaagact | gacgctcagg | tgcgaaagcg | | 770 |

<210> SEQ ID NO 2
<211> LENGTH: 700
<212> TYPE: DNA
<213> ORGANISM: Escherichia coli

<400> SEQUENCE: 2

| | | | | | |
|---|---|---|---|---|---|
| ggttaaaccg | cctggctgtg | gatgaatgct | attttttaaga | cttttgccaa | actggcggat | 60 |
| gtagcgaaac | tgcacaaatc | cggtgcgaaa | agtgaaccaa | caacctgcgc | cgaagagcag | 120 |
| gtaaatcatt | accgatcccc | aaaggacgct | gttaataaag | gagaaaaaat | ctggcatgca | 180 |
| tatccctctt | attgccggtc | gcgatgactt | tcctgtgtaa | acgttaccaa | ttgtttaaga | 240 |
| agtatatacg | ctacgaggta | cttgataact | tctgcgtagc | atacatgagg | ttttgtataa | 300 |
| aaatggcggg | cgatatcaac | gcagtgtcag | aaatccgaaa | cagtctcgcc | tggcgataac | 360 |
| cgtcttgtcg | gcggttgcgc | tgacgttgcg | tcgtgatatc | atcagggcag | accggttaca | 420 |
| tccccctaac | aagctgttta | agagaaaata | ctatcatgac | ggacaaattg | acctcccttc | 480 |
| gtcagtacac | caccgtagtg | gccgacactg | gggacatcgc | ggcaatgaag | ctgtatcaac | 540 |
| cgcaggatgc | cacaaccaac | ccttctctca | ttcttaacgc | agcgcagatt | ccggaatacc | 600 |
| gtaagttgat | tgatgatgct | gtcgcctggg | cgaaacagca | gagcaacgat | cgcgcgcagc | 660 |
| agatcgtgga | cgcgaccgac | aaactggccg | taaatattgg | | | 700 |

<210> SEQ ID NO 3
<211> LENGTH: 539
<212> TYPE: DNA
<213> ORGANISM: Klebsiella pneumoniae

<400> SEQUENCE: 3

| | | | | | |
|---|---|---|---|---|---|
| atcctggctc | agattgaacg | ctggcggcag | gcctaacaca | tgcaagtcga | gcggtagcac | 60 |
| agagagcttg | ctctcgggtg | acgagcggcg | gacgggtgag | taatgtctgg | gaaactgcct | 120 |

```
gatggagggg gataactact ggaaacggta gctaataccg cataacgtcg caagaccaaa        180
gtgggggacc ttcgggcctc atgccatcag atgtgcccag atgggattag ctagtaggtg        240
gggtaacggc tcacctaggc gacgatccct agctggtctg agaggatgac cagccacact        300
ggaactgaga cacggtccag actcctacgg gaggcagcag tggggaatat tgcacaatgg        360
gcgcaagcct gatgcagcca tgccgcgtgt gtgaagaagg ccttcgggtt gtaaagcact        420
ttcagcgggg aggaaggcga tgaggttaat aacctcgtcg attgacgtta cccgcagaag        480
aagcaccggc taactccgtg ccagcagccg cggtaatacg gagggtgcaa gcgttaatc        539
```

```
<210> SEQ ID NO 4
<211> LENGTH: 770
<212> TYPE: DNA
<213> ORGANISM: Klebsiella pneumoniae
<220> FEATURE:
<221> NAME/KEY: misc_feature
<222> LOCATION: (432)..(432)
<223> OTHER INFORMATION: n is a, c, g, or t

<400> SEQUENCE: 4
ggcaggccta acacatgcaa gtcgagcggt agcacagaga gcttgctctc gggtgacgag        60
cggcggacgg gtgagtaatg tctgggaaac tgcctgatgg agggggataa ctactggaaa       120
cggtagctaa taccgcataa tgtcgcaaga ccaaagtggg ggaccttcgg gcctcatgcc       180
atcagatgtg cccagatggg attagctagt aggtggggta acggctcacc taggcgacga       240
tccctagctg gtctgagagg atgaccagcc acactggaac tgagacacgg tccagactcc       300
tacgggaggc agcagtgggg aatattgcac aatgggcgca agcctgatgc agccatgccg       360
cgtgtgtgaa gaaggccttc gggttgtaaa gcactttcag cggggaggaa ggcgatgagg       420 ttaataaccct tntcgattga cgttacccgc agaagaagca ccggctaact ccgtgccagc       480
agccgcggta atacgagggg tgcaagcgtt aatcggaatt actgggcgta aagcgcacgc       540
aggcggtctg tcaagtcgga tgtgaaatcc ccgggctcaa cctgggaact gcattcgaaa       600
ctggcaggct agagtcttgt agaggggggt agaattccag gtgtagcggt gaaatgcgta       660
gagatctgga ggaataccgg tggcgaaggc ggcccctgg acaaagactg acgctcaggt        720
gcgaaagcgt ggggagcaaa caggattaga taccctggta gtccacgccg                  770
```

```
<210> SEQ ID NO 5
<211> LENGTH: 617
<212> TYPE: DNA
<213> ORGANISM: Klebsiella pneumoniae

<400> SEQUENCE: 5
tgaacgctgg cggcaggcct aacacatgca agtcgagcgg tagcacagag agcttgctct        60
cgggtgacga gcggcggacg ggtgagtaat gtctgggaaa ctgcctgatg gaggggggata      120 actactggaa acggtagcta ataccgcata aygtcgcaag accaaagtgg gggaccttcg       180
ggcctcatgc catcagatgt gcccagatgg gattagctag taggtggggt aacggctcac       240
ctaggcgacg atccctagct ggtctgagag gatgaccagc cacactggaa ctgagacacg       300
gtccagactc ctacgggagg cagcagtggg gaatattgca caatgggcgc aagcctgatg       360
cagccatgcc gcgtgtgtga agaaggcctt cggttgtaa agcactttca gcggggagga       420
aggcgatgag gttaataacc tyatcgattg acgttacccg cagaagaagc accggctaac       480
tccgtgccag cagccgcggt aatacggagg gtgcaagcgt taatcggaat tactgggcgt       540
```

```
aaagcgcacg caggcggtct gtcaagtcgg atgtgaaatc cccgggctca acctgggaac    600
tgcattcgaa actggca                                                  617

<210> SEQ ID NO 6
<211> LENGTH: 693
<212> TYPE: DNA
<213> ORGANISM: Klebsiella pneumoniae
<220> FEATURE:
<221> NAME/KEY: misc_feature
<222> LOCATION: (149)..(149)
<223> OTHER INFORMATION: n is a, c, g, or t

<400> SEQUENCE: 6
acgctggcgg caggcctaac acatgcaagt cgagcggtag cacagagagc ttgctctcgg     60
gtgacgagcg gcggacgggt gagtaatgtc tgggaaactg cctgatggag gggataact    120 actgaaaacg gtagctaata ccgcataang tcgcaagacc aaagtggggg accttcgggc   180
ctcatgccat cagatgtgcc cagatgggat tagctagtag gtggggtaac ggctcaccta   240
ggcgacgatc cctagctggt ctgagaggat gaccagccac actggaactg agacacggtc   300
cagactccta cgggaggcag cagtgggaa tattgcacaa tgggcgcaag cctgatgcag    360
ccatgccgcg tgtgtgaaga aggccttcgg gttgtaaagc actttcagcg gggaggaagg   420
cgatgaggtt aataacctca tcgattgacg ttacccgcag aagaagcacc ggctaactcc   480
gtgccagcag ccgcggtaat acggagggtg caagcgttaa tcggaattac tgggcgtaaa   540
gcgcacgcag gcggtctgtc aagtcggatg tgaaatcccc gggctcaacc tgggaactgc   600
attcgaaact gcaggctag agtcttgtag aggggggtag aattccaggt gtagcggtga   660
aatgcgtaga gatctggagg aataccggtg gcg                                693

<210> SEQ ID NO 7
<211> LENGTH: 294
<212> TYPE: DNA
<213> ORGANISM: Staphylococcus saprophyticus

<400> SEQUENCE: 7
atgattgcag tacaagattt agatgattta gacgcagatt atatcgctgt tcatactggt    60
tatgacttac aagctgaagg tcaatctcct ttagaaagtt tacgtaaagt taaatctgta   120
attagtaatt ctaaagtagc agtcgcaggt ggtattaaac cagatacaat taaagatatt   180
gttgcagaaa atcctgattt aattattgtt ggtggcggca ttgcaaatgc tgatgaccct   240
gtagaagctg ctaaacaatg tcgtgatatt gtagatgccc atacaaatgc ataa         294

<210> SEQ ID NO 8
<211> LENGTH: 456
<212> TYPE: DNA
<213> ORGANISM: Staphylococcus saprophyticus

<400> SEQUENCE: 8
atggagcata aagagggaaa cttagaaata ataattaacc aattctatga tgctacagcg    60
aatattaata aagcaattac taacatggtt aaagaattgg aaccaggtcg ttacttatct   120
tatgaacaaa tagaaacaat gtattttatt cagcataatg aaaagtatc gattaacgac    180 ttagcaaata gcaacgtac ttataagaca gctgcatcaa aacgtgttaa gaagttagaa    240
agcaaaggtt atgtgcaacg agtttattcg aatgataaac gtactaaatt attgagtttg   300
acgcataatg gagaacgctt attaaaagaa atgaaaataa acttaacaaa agaaataaag   360
```

-continued

| | |
|---|---|
| ttactttttgt taagttgttt tgttagagaa gattttgaaa aatttatgta tcagctcatg | 420 |
| aattttgaaa agacattttt aaaaaagtac tactag | 456 |

<210> SEQ ID NO 9
<211> LENGTH: 360
<212> TYPE: DNA
<213> ORGANISM: Enterococcus spp

<400> SEQUENCE: 9

| | |
|---|---|
| tacttgtacc actggatgag cagcgaacgg tgagtacgcg tgggatctgc ctttgagcgg | 60 |
| ggacacattt ggaacgaatg ctaataccgc ataaaacttt aacacaagtt ttaagtttga | 120 |
| agatgcattg catcactcag atgatcccgc gttgtattag ctagtggtga ggtaaagctc | 180 |
| accaaggcga tgatacatta gccgacctga gaggtgatcg cacaatggac tgagacacgg | 240 |
| cccaactcct acggggggcgc gtagggaatc ttcggcaatg acgaagtctg accgagcacg | 300 |
| cccgtgagtg aagaagttttt cggatctaaa ctctgtggta gagaagaaca tcggtgagag | 360 |

<210> SEQ ID NO 10
<211> LENGTH: 519
<212> TYPE: DNA
<213> ORGANISM: Enterococcus spp

<400> SEQUENCE: 10

| | |
|---|---|
| attcatgact ggggtgaagt cgtaacaagg taaccgtagg ggaacctgcg gttggatcac | 60 |
| ctccttacct gaagatacga aatattgtgt agtgctcaca cagattgtct gataagtgtc | 120 |
| acgagcaaat accttatgca ggcttgtagc tcaggtggtt agagcgcacc cctgataagg | 180 |
| gtgaagtcgg tggttcgagt ccactcaggc ctaccaactc ccttcctgtg tgaagcggac | 240 |
| ggtggtaata aggtattgca gtaaagtcat ggggctatag ctcagctggg agagcgcctg | 300 |
| cttttgcacgc aggaggttct gcggttcgat cccgcatagc tccaccatat ttcagaacat | 360 |
| actgagaaat cagcatgttg tgaaatattt tgctctttaa caatctggaa caagctgaaa | 420 |
| ttcgaaaaca ctcggattgc ttttaataaa gtgatccgag agtctctcaa atgcttacag | 480 |
| cacgaagtga aacaccttcg ggttgtgagg ttaatgtga | 519 |

<210> SEQ ID NO 11
<211> LENGTH: 542
<212> TYPE: DNA
<213> ORGANISM: Proteus mirabilis

<400> SEQUENCE: 11

| | |
|---|---|
| ttgaacgctg gcggcaggcc taacacatgc aagtcgagcg gtaacaggag aaagcttgct | 60 |
| ttcttgctga cgagcggcgg acgggtgagt aatgtatggg gatctgcccg atagagggg | 120 |
| ataactactg gaaacggtgg ctaataccgc atgatgtcta cggaccaaag caggggctct | 180 |
| tcggaccttg cgctatcgga tgaacccata tgggattagc tagtaggtgg ggtaatggct | 240 |
| cacctaggcg acgatctcta gctggtctga gaggatgatc agccacactg ggactgagac | 300 |
| acggcccaga ctcctacggg aggcagcagt ggggaatatt gcacaatggg cgcaagcctg | 360 |
| atgcagccat gccgcgtgta tgaagaaggc cttaggggttg taaagtactt tcagcgggga | 420 |
| ggaaggtgtt aagattaata ctcttagcaa ttgacgttac ccgcagaaga agcaccggct | 480 |
| aactccgtgc cagcagccgc ggtaatacgg agggtgcaag cgttaatcgg aattactggg | 540 |
| cg | 542 |

<210> SEQ ID NO 12
<211> LENGTH: 420
<212> TYPE: DNA
<213> ORGANISM: Proteus mirabilis

<400> SEQUENCE: 12

```
aggatgagtt acctgccact gaatttagta tgtggatacg tcccttgcag gcagaactaa      60
gcgataacac gctggcactg tatgcaccta atcgttttgt gttagattgg gtaagagaaa     120
agtacattaa taatattaat gcattattag tcgactttg tggttctgat gtcccttcgc      180
tgcgttttga agtgggaaat aaacctgtat cagcacgtac caccgagagt gttcccaaaa     240
ccgtgacaca tcccgcggtt aattccacac cgactaacag ccagccggtg cgtcctagct     300
gggataatca accgcaatcc cagttacctg aacttaatta tcgttctaat gttaatccta     360
agcataaatt tgataatttc gttgaaggta atcgaaccaa acttgctaga gcagccgcaa     420
```

<210> SEQ ID NO 13
<211> LENGTH: 1120
<212> TYPE: DNA
<213> ORGANISM: Pseudomonas aeruginosa

<400> SEQUENCE: 13

```
atagatacaa ggaagtcatt tttcttttaa aggatagaaa cggttaatgc tcttgggacg      60
gcgcttttct gtgcataact cgatgaagcc cagcaattgc gtgttctcc ggcaggcaaa      120
aggttgtcga gaaccggtgt cgacgctgtt tccttcctga gcgaagcctg gggatgaacg     180
agatggttat ccacagcggt ttttccaca cggctgtgcg cagggatgta cccccttcaa      240
agcaagggtt atccacaaag tccaggacga ccgtccgtcg gcctgcctgc ttttattaag     300
gtcttgattt gcttgggcc tcagcgcatc ggcatgtgga taagtccggc ccgtccggct      360
acaataggcg cttatttcgt tgtgccgcct ttccaatctt tgggggatat ccgtgtccgt     420
ggaactttgg cagcagtgcg tggatcttct ccgcgatgag ctgccgtccc aacaattcaa     480
cacctggatc cgtcccttgc aggtcgaagc cgaaggcgac gaattgcgtg tgtatgcacc     540
caaccgtttc gtcctcgatt gggtgaacga gaaataccctc ggtcggcttc tggaactgct     600
cggtgaacgc ggcgagggtc agttgcccgc gctttcctta ttaataggca gcaagcgtag     660
ccgtacgccg cgcgccgcca tcgtcccatc gcagacccac gtggctcccc cgcctccggt     720
tgctccgccg ccggcgccag tgcagccggt atcggccgcg cccgtggtag tgccacgtga     780
agagctgccg ccagtgacga cggctcccag cgtgtcgagc gatccctatg agccggaaga     840
acccagcatc gatccgctgg ccgccgccat gccggccgga gcagcgcctg cggtgcgcac     900
cgagcgcaac gtccaggtcg aaggtgcgct gaagcacacc agctatctca accgtacctt     960
caccttcgag aacttcgtcg agggcaagtc caaccagttg gcccgcgccg ccgcctggca    1020
ggtggcggac aacctcaagc acggctacaa cccgctgttc ctctacggtg gcgtcggtct    1080
gggcaagacc cacctgatgc atgcggtggg caaccacctg                         1120
```

<210> SEQ ID NO 14
<211> LENGTH: 1050
<212> TYPE: DNA
<213> ORGANISM: Pseudomonas aeruginosa

<400> SEQUENCE: 14

```
ttggcgttgg ccgggtcgag cttgcccagt tcgcgggcga tggtgttgac ctgggtgatc      60
gaggcgctga tggacaggaa ggtgtgcggg ttgaccacct tgccggcgcc gcgcgcggcc     120
```

| | |
|---|---|
| atgccggtgg cggccagcag cggcaccttg gcgttcgcct cgatcaccgg gatgccgggc | 180 |
| ttttcgctgg aggcgatcat gcgctcggcg aaatcgtcgt ggccgacgcc gttgagcacc | 240 |
| accacgtcga gcgtgccgat gcgcttgatg tcctcggcgc gcggctcgta ggcatgcggg | 300 |
| ttgaaaccgg cggggatcag cggcaccacc tcggccttgt cgccgacgat gttgctcacg | 360 |
| tagctgtagt agggatgcag ggtgatgccg atgcgcaggc gcttgccgtc ttcggcctgg | 420 |
| gccagcgggg cgagcagggc cagcagcagg cggccagca gggcacggcc cgggaggagg | 480 |
| gcggcgaggc cgcgcggacg ggatgagcga cgggagaaca gcatggaaaa acgccttctg | 540 |
| tggagtcgat gtgcgatcaa tggcggtgct gacgggtcac gccggcgtcg aagcggctga | 600 |
| ccacctggcg ccagccggcg tcggccaggg ctcgggcgtc gcccggtacg cgccggcag | 660 |
| cggccgtggc gggcttcagc cagacttcgg cggggccgag cagcaggagg aacgagccgg | 720 |
| ccacctcggg cttgccgctg acgcccaggt agctcggacg cccggcggtt tcgccgtggc | 780 |
| tccagcggtg ctcgccgcgg ctgcttgcgg cgacgtcggc gacgaagggc gggaagccct | 840 |
| cggcggccag ttcgtcgacg gagggcgcgg cttcgccgtc gtccaggcgc gcctggatat | 900 |
| cttcggcggc gacctgcagg tcggcgtaga tgccctgttc ggcggcattc aggtcgagcc | 960 |
| gggcgtccac ctggtgggcg tccagggctt gcgcttcatg ggactgctgg cgcagcccga | 1020 |
| ccaccgtggc ggcgagggcc aggatcagca | 1050 |

<210> SEQ ID NO 15
<211> LENGTH: 774
<212> TYPE: DNA
<213> ORGANISM: Staphylococcus aureus

<400> SEQUENCE: 15

| | |
|---|---|
| aggatgaacg ctggcggcgt gcctaataca tgcaagtcga gcgaacggac gagaagcttg | 60 |
| cttctctgat gttagcggcg gacgggtgag taacacgtgg ataacctacc tataagactg | 120 |
| ggataacttc gggaaaccgg agctaatacc ggataatatt ttgaaccgca tggttcaaaa | 180 |
| gtgaaagacg gtcttgctgt cacttataga tggatccgcg ctgcattagc tagttggtaa | 240 |
| ggtaacggct taccaaggca acgatgcata gccgacctga gagggtgatc ggccacactg | 300 |
| gaactgagac acggtccaga ctcctacggg aggcagcagt agggaatctt ccgcaatggg | 360 |
| cgaaagcctg acggagcaac gccgcgtgag tgatgaaggt cttcggatcg taaaactctg | 420 |
| ttattaggga agaacatatg tgtaagtaac tgtgcacatc ttgacggtac ctaatcagaa | 480 |
| agccacggct aactacgtgc cagcagccgc ggtaatacgt aggtggcaag cgttatccgg | 540 |
| aattattggg cgtaaagcgc gcgtaggcgg ttttttaagt ctgatgtgaa agcccacggc | 600 |
| tcaaccgtgg agggtcattg gaaactggaa aacttgagtg cagaagagga aagtggaatt | 660 |
| ccatgtgtag cggtgaaatg cgcagagata tggaggaaca ccagtggcga aggcgacttt | 720 |
| ctggtctgta actgacgctg atgtgcgaaa gcgtggggat caaacaggat taga | 774 |

<210> SEQ ID NO 16
<211> LENGTH: 1555
<212> TYPE: DNA
<213> ORGANISM: Staphylococcus aureus

<400> SEQUENCE: 16

| | |
|---|---|
| ttttatggag agtttgatcc tggctcagga tgaacgctgg cggcgtgcct aatacatgca | 60 |
| agtcgagcga acggacgaga agcttgcttc tctgatgtta gcggcggacg ggtgagtaac | 120 |
| acgtggataa cctacctata agactgggat aacttcggga aaccggagct aataccggat | 180 |

```
aatatttttga accgcatggt tcaaaagtga aagacggtct tgctgtcact tatagatgga    240
tccgcgctgc attagctagt tggtaaggta acggcttacc aaggcaacga tacgtagccg    300
acctgagagg gtgatcggcc acactggaac tgagacacgg tccagactcc tacgggaggc    360
agcagtaggg aatcttccgc aatgggcgaa agcctgacgg agcaacgccg cgtgagtgat    420
gaaggtcttc ggatcgtaaa actctgttat tagggaagaa catatgtgta agtaactgtg    480
cacatcttga cggtacctaa tcagaaagcc acggctaact acgtgccagc agccgcggta    540
atacgtaggt ggcaagcgtt atccggaatt attgggcgta aagcgcgcgt aggcggtttt    600
ttaagtctga tgtgaaagcc cacggctcaa ccgtggaggg tcattggaaa ctggaaaact    660
tgagtgcaga agaggaaagt ggaattccat gtgtagcggt gaaatgcgca gagatatgga    720
ggaacaccag tggcgaaggc gactttctgg tctgtaactg acgctgatgt gcgaaagcgt    780
ggggatcaaa caggattaga taccctggta gtccacgccg taaacgatga gtgctaagtg    840 ttaggggggtt ccgcccctt agtgctgcag ctaacgcatt aagcactccg cctggggagt    900
acgaccgcaa ggttgaaact caaaggaatt gacgggggacc cgcacaagcg gtggagcatg    960
tggtttaatt cgaagcaacg cgaagaacct taccaaatct tgacatcctt tgacaactct   1020
agagatagag ccttccccctt cggggggacaa agtgacaggt ggtgcatggt tgtcgtcagc   1080
tcgtgtcgtg agatgttggg ttaagtcccg caacgagcgc aacccttaag cttagttgcc   1140
atcattaagt tgggcactct aagttgactg ccggtgacaa accggaggaa ggtgggggatg   1200 acgtcaaatc atcatgcccc ttatgattttg ggctacacac gtgctacaat ggacaataca   1260
aagggcagcg aaaccgcgag gtcaagcaaa tcccataaag ttgttctcag ttcggattgt   1320
agtctgcaac tcgactacat gaagctggaa tcgctagtaa tcgtagatca gcatgctacg   1380
gtgaatacgt tcccgggtat tgtacacacc gcccgtcaca ccacgagagt ttgtaacacc   1440
cgaagccggt ggagtaacct tttaggagct agccgtcgaa ggtgggacaa atgattgggg   1500
tgaagtcgta acaaggtagc cgtatcggaa ggtgcggctg gatcacctcc tttct         1555
```

<210> SEQ ID NO 17
<211> LENGTH: 1491
<212> TYPE: DNA
<213> ORGANISM: Candida spp

<400> SEQUENCE: 17

```
gctggaaaaa cgtctccaaa tcacattcct taagcaatta tctcatatcg gaaacagaat     60
atatacaaca acgcctggaa tgcagcataa acaatttaa atctttccat cccaccagat    120
tcaacctctt gttctctttc aaggataaac ttgttcaacc atccaacaag ataactaact    180
ataaacacaa cttggtgacg cgataacccc ttggctcgtg caatatacga cgacaaatac    240
tgcatcgctt tcaatcgttt ctccaaaatc tccgtagggt taaatgcaac atcaatcaac    300
aagaccaaaa acgaatcagc caactcaggt tggtactggg taacatgaaa caacacaaac    360
tgaatcagct tcgtaaaatg tgttgggagt atatgactct tgaataatga gttaatagta    420
ttgaacaaat taaccccatt gccgttattc aactcttcaa gagtgaatga gtctctggtc    480
gacgtcaaca ataaactaat cacactgtca agcttgttca gcaacgattt gatatctgta    540
gtaggagcag taacccattc ctcgtcgtca ctctcatcat cactctcgtc atcaccactc    600
tcgtcatctc cactctcatc atcactttca tcctcactat cactggccac ttcgtcttct    660
tcatcgttca acaattcttc aatctcttca tcatcaacat catcaagtga tgtctgcaaa    720
tctgtatcca ttttgatcga cgactcaata atcatttgcc agatttcaaa ttgcaactcg    780
```

```
ggacagtaac gtattatctt aacaaggttg tgcacataat tagtcaattc actattacta    840
gacgatatat gatgagggaa attcttctgc aacacctgtg gaatcatact aatagaagtg    900
gggatatact tgataatctt gatcaacacc tcgtggtggg tatccacatc ctgtctgtca    960
aactctctaa ccaacttgct cataacttca tgcaaatatt taggtaatgt cgataccaat   1020
gcaactaaaa actgggaata catttccaca aacctgctat acccatcacg atgtttcaca   1080
tccatccatc gatactcaag aatggcaaaa atcatattat gacacgcctt gttatccaac   1140
cgtgacgtat tcgaagccaa tgatctaaga actatggaga aatgacttat gctaatggct   1200
tctttattgc caatggggag acttatctta tcagtgatgg tatttatctg aactggatca   1260
tccttctcca atgcagattt cacatacgac gagtacatct tttctgaaaa ctcatcatca   1320
ctcatcgtat tctgtttctt attcgggagg tcttcagtgg taatacctct tttcgtgaa    1380 acttcaagag acatcatatg ttatagagat gggggagtaa aagagaagaa ggagaaaaaa   1440
tttttttttt tttttttttt tttttttata cgataaactt tttggagcta c            1491
```

<210> SEQ ID NO 18
<211> LENGTH: 1190
<212> TYPE: DNA
<213> ORGANISM: Candida spp

<400> SEQUENCE: 18

```
aagtttccca tcaagagcac caccgtcgta tccaaaatcc gcaaacatct ccttagtctc     60
ctttggattg gcaatagcca tttgcatatt aacagctaaa tggccccctg cagaatcacc    120
aataagatgt atatccttaa acccagcttt gattaaattg gtataactct caagactctc    180
caccaattgt gctggaaata catgatcaaa aagtgtcaac aggtaatcaa caaccaaaat    240
agacaactca tcagcaaccc ttgcatccaa tgcataatgc aacgcagcaa tagaaaccaa    300
ctgcgattta aacaaattca acaaatacc accaccatga aggtaaacca aaactttacc     360
cgatggattg tcactcttgt ggatccaata cgaacgggca tcaaactttt ccccaaaccc    420
attcaaagat ttaaccatag gattttttggc aacttgctta acaccttct caactggctc     480 ataaacaaca gccttgacgt tttgcttctt gtaattacca ctcatatgat attctaccga    540
taacaacaca ttcttccaca agaattgcg aaactcaatg tttgtacgac tatagatggt      600
acccacagtg taatactgca atacagcctt gatcaccaca tacggtaaac taagtaactt    660
ggccaaaaag tcaatgctaa tcatggtttg gtggttgaac aaaagaaac ctttctttta      720 attggttttt cttttctcgt tgttcaaaaa agaaaaaaa aaaaaatttt ccacgaggaa     780
cacttttcga gaacaaaaag aaaagcaaaa tgcttttttgt acaatcggcc ataaaacgcg    840
tgtacctgaa tcattcaatt agtagtatag ggggagatat aaccaatatg tgtatgcatc    900
acgttttccc agcacgtgcc acgcacacat ttctaattt tgttggctta tcttatcttc     960
ccggatcccc gcttccgcac tttaatttcg gcaatttctc aattagtcat ttttcacttg    1020
tcgcctaaag tagacaaatt tttttttttct tcctctttcc gcagcgttat aaattcctac   1080
atttcttccc ccagaaaaat caacaaccag ctactcacca aacagctact caccaaacaa   1140
ccaactatca aactaccctc catgacagca tctacaaaag ccaaagactt                1190
```

<210> SEQ ID NO 19
<211> LENGTH: 1190
<212> TYPE: DNA
<213> ORGANISM: Candida albicans

<400> SEQUENCE: 19

```
ctggttgttg aagaagaaaa gtgatgtttt ctgccatctt ttttttgcca tcttttttttt    60
tctgtcagct ttttttctgc catcttttttt tgttgacgtg tcccysgctc accgatcacc    120
cacgggtctc ccaccggcac cccgattttc acaactacac aatcaactgc ctccaaaaca    180
gtcaaataac ttacccacta aacttcacaa tagagtcgca acktaatag ttsttctgac     240
ttgtttagct gtttctaaat ttaacttttg ccatcttaaa ctcaaaaata gacttccctt    300
actcctttca gtaaattcta ttctcctgct tcttctttga agttaattct cttactatac    360
acaattacaa gtctaaaact ctattatttg ctgtgcatca attctttgtt tgaatttccc    420
cattttcacc ccaactagaa ccaactttta gctcagaatt tttgcaaact cgagcccaaa    480
atttcctct cctcggaaat racttattcc cgaaaatggy aaaaaatgtc gtcgcctcaa     540
aaagatggc aaaaatccc catacaaaat taaagatgac aaaaaatgtc gcaccaccaa      600
aaaaagatg gcaaaatat gtcgcaccac caaaaaaaag tcgcatagtt aaaaaaaaga     660
tgacaaaaaa atgtcgtaaa atcggccaaa actgactaaa acgggctcta gctcaacacc    720
caaaagaggt atcgacttct aaccttgata ggtagaatct acagagtgag agcwatctas    780
tggtgcttta aaaagtrcaa aaagtgggca tctacctact gtttttccgc cttttctgtt    840
ctcccacctt taaccgcgca tatctcggca accagtgctc cgtttgctcy caaacacagc    900
ccatcctatt cctacacccc taaacaacct atataagcct aaaaaaaacc ccaaaaaaac    960
cccaaaaaaa cttggtaaat ttttgtcatc tttttttgac agcttgtaaa atctttgcca    1020
tcttttttt cgcgcctaac aaaatttgtt agcaaaaaaa ttttttgccat ctttttttccg   1080
cgtttccatt agtatggaac aacacggggg gtccttgtag gttgtgttga tagagcaggt   1140
agagcaggta gagatgtgtt cgtatttttg cgcgtatttg cgcattgtgg               1190
```

<210> SEQ ID NO 20
<211> LENGTH: 961
<212> TYPE: DNA
<213> ORGANISM: Candida albicans

<400> SEQUENCE: 20

```
ggtgttgttg cgcattttttt ctgttgacca cggatgtcta acttcaagcg agcacccgag    60
caaagcgaga gtcacacaaa caagtttaga tttagcaata attttctagc caatacaggc    120
cacacacctc gagtgagcag cacttctcaa actgccgcac cacaaccgta cggatgctca    180
cctttttttt tttttttcttt tttggggtgc ttgcacccc aatagtccgg atgtgtgtga    240
gaatgagttg ggtgtgcgga tgctttagat agttgattga ccgtacggat gtttaaattg    300
ggtagtgtgt tgtttaatta gagattggtt tatttgagag agttgtaatt taggttcgag    360
gagttgttga ggtatagagt atttcaaaat aggaatgttg ttccaaacta gggggttgt     420
tcaattaggt atgaaagtgg ttcaaatcag tgaataagtt taattttgat atagtttttc    480
aatctcagag tagttccaat ttgaagagag ttctagattg gtgtagttgt tttagagtta    540
gtgttgagag atgtttaaat caagggtagt tccggtacag tgatttgtac aaagtcagag    600
tagttgtaaa cgagaagaga gttttaaact attggggttg ttgttcaatt agaaaattggt   660
ttatttgaga gagttgtaat ttgggttcag ggagttgttg aaattccgag tggctcattt    720
cagaagagag ttccaaacta gtgttgttgt tgaattagtt ttaagagtgg tctaaatcaa    780
gggttgagtt cttggttcag ggagttgctc aaacttagag ttgctcattt gtgaagagag    840
ttctaaatag attgtacagt tattcaaatt tatcacccgg ttaatacatt tgttgaaatt    900
```

| | |
|---|---:|
| agctattcac tcaaccaaaa ataaaatttt tttttagct ttcaaccaaa aaagcaatag | 960 |
| t | 961 |

<210> SEQ ID NO 21
<211> LENGTH: 1050
<212> TYPE: DNA
<213> ORGANISM: Chlamydia trachomatis

<400> SEQUENCE: 21

| | |
|---|---:|
| tcaaagtttt gtgtttccaa agctttaata ataagagcta caggaaccgg gattgctgaa | 60 |
| acacgctcat agatttcagc atcaataatg ggccgttttt ctccatgcat gttggtatcc | 120 |
| atatccatga agacccgttt tctcttgaaa aaaccagata gataggttcg tgtgactgta | 180 |
| agtttattcc aacctaagcg caagaaactg aaagattcac gagttttagg attaggaagg | 240 |
| agtgttatgg tatggtctct catacctaaa caaggatttt cttcttttt acataatctt | 300 |
| cctgtaagag gatctccaga ataagggta atctcatcgg aagagaaaat gtctttagga | 360 |
| agaagatcag agaaactagc gcctttcgca gtaatgagat attttctttg agaaggagga | 420 |
| agagctgatc ctgctaaggc aacgatttgt tgtcctaaaa caaagccttt taaaaataga | 480 |
| tgccctatag ataacacctc ttggaagcta atagtaaaca caacatctct ttcgtttcga | 540 |
| atacgagcga tgtgatgaat gtgcgttgaa ggagatcctg atgggaaggg gccatctatt | 600 |
| gtgtgtaagt gggctatgga tacgagatcc tgggttggga gagttagtct gtctgtagaa | 660 |
| atgatatgag gcttcagtcc aaatagtttt gctattgcct gaactcccac aacaaaaatg | 720 |
| taataaccat cttctttga agaaaaaaga ctgagatgtt tttccacaga aggggtgaaa | 780 |
| gggcgattat ccgctaagtt aataaaaaca tctcgaggag attgtgttgg aagagctggg | 840 |
| atatcaaaag gtctttgttt gaaaagagcg aaaagacctt cctttttaaa aacttctaaa | 900 |
| agatcttttt gagtcaaaga ttgaagatca taagaaaact tagtttgaga aataccaggc | 960 |
| ttcttcttga tgacgatctc taaaagagca cgtttatttc ctctacggat ctctacaacc | 1020 |
| tctccatcaa caggagaggt aataaacact | 1050 |

<210> SEQ ID NO 22
<211> LENGTH: 700
<212> TYPE: DNA
<213> ORGANISM: Chlamydia trachomatis

<400> SEQUENCE: 22

| | |
|---|---:|
| cttgattttg taagagatca tacaggtgga tcgcgcggat caagtaagat tctggagagg | 60 |
| aaaaaggagg gaggataggc tcaatgtcat gaggtgtaac gcggaggatg gtagcttctt | 120 |
| taggaagtag atgagaggct tgtagtaacg ctaaggatag gtaggattct aaataagatt | 180 |
| ctagttcaaa ggcatcttta gggaatccat gagttttctg agttttctta aaggcttctc | 240 |
| ccggatgcat agaaaataga tatacccctt ttgaacatac gccatgaatc gtcccttgaa | 300 |
| gatgaatatt tttaggggg agagatagga gtagaggagg gacttgttga tcattaggat | 360 |
| ggagtgggtc gtgaaaaagt tgatcggaaa atacaacaga aaggggggtt gtagcaggat | 420 |
| cttttctgcaa agtttctaag cgtttactta cagagtcttg tacatcggtg tatagagatt | 480 |
| ctgtaaaggc tgaaagataa ttagtagtgg gtagaggagt tttagaagag agaaggtggt | 540 |
| tccaaaaagc tttagcatcg tgaggactag gaaagacttt ttctgattta gaaaatagtg | 600 |
| ctttgggatt aaaggaaaag ccatgttgcg tgcttaggaa aaagtttaaa ggatctttga | 660 |
| aagctttgat tagatgttgt agggataggt gtgaaggtaa | 700 |

<210> SEQ ID NO 23
<211> LENGTH: 840
<212> TYPE: DNA
<213> ORGANISM: Mycoplasma genitalium

<400> SEQUENCE: 23

| | | | | | |
|---|---|---|---|---|---|
| agtaagaatg | ttactgctta | cacccccttc | gccacccca | tcaccgattc | taaaagtgat | 60 |
| ctggttagtt | tggcacaact | tgattcttct | tatcaaatcg | ctgaccaaac | catccataac | 120 |
| accaacttgt | ttgtgttgtt | caagtccaag | gatgtgaagc | ttacatatag | ttcaagtggc | 180 |
| tcaaataacc | agattagttt | tgattcaact | agtcaaggtg | aaaaaccatc | ctatgtggtc | 240 |
| gagtttacta | actctaccaa | cattggcatc | aagtgaagcg | tggtgaaaaa | gtatcagtta | 300 |
| gatctaccaa | atgttaccaa | tgagatgaac | caagtgttgc | aagaattgat | cctagaacaa | 360 |
| ccccttacca | agtataccctt | aaacagtagt | ttggctaaac | aaaagggcaa | agccagata | 420 |
| gaggtacatc | ttggttcaaa | ttcaaatcag | tgacaatcga | tgcgtaatca | acatgaccta | 480 |
| aacaacaatc | ccagcccaa | tgcttcaact | gggtttaaac | tcactaccgg | caacgcatat | 540 |
| agaaaattaa | atgagtcctg | accaatttat | caaccaattg | atgggaccaa | gcagggcaaa | 600 |
| ggaaggata | gtagtgggtg | gagttcaaca | gaagcaacaa | cggcaaaaaa | tgatgcgccc | 660 |
| agtgtttctg | gaagtggaac | atcagacacc | gcttcaaaat | tcaaaagtta | cctcaacacc | 720 |
| aagcaagcgt | tagagagcat | cggcatcttg | tttgatgggg | atggaatgag | gaatgtggtt | 780 |
| acccagctct | attatgcttc | tactagcaag | ctagcagtca | ccaacaacca | cattgtcgtg | 840 |

<210> SEQ ID NO 24
<211> LENGTH: 1483
<212> TYPE: DNA
<213> ORGANISM: Mycoplasma genitalium

<400> SEQUENCE: 24

| | | | | | |
|---|---|---|---|---|---|
| agtaagaatg | ttactgctta | cacccccttc | gccacccca | tcaccgattc | taaaagtgat | 60 |
| ctggttagtt | tggcacaact | tgattcttct | tatcaaatcg | ctgaccaaac | catccataac | 120 |
| accaacttgt | ttgtgttgtt | caagtccaag | gatgtgaagc | ttacatatag | ttcaagtggc | 180 |
| tcaaataacc | agattagttt | tgattcaact | agtcaaggtg | aaaaaccctc | ctatgtggtc | 240 |
| gagtttacta | actctaccaa | cattggcatc | aagtgaacga | tggtgaaaaa | gtatcagtta | 300 |
| gatgtaccga | atgtaagtag | tgacatgaac | caagtgttgc | aagaattgat | ccttgaacaa | 360 |
| cctttgacta | agtatacgct | taatagtagt | ttggccaaag | agaagggcaa | aagccaaagg | 420 |
| gaggtgcatc | tgggttcaaa | ttcaaatcag | tgacaatcga | tgcgtaatca | acatgaccta | 480 |
| aacaacaatc | ccagcccaa | tgcttcaact | ggatttaaac | tcactaccgg | caacgcatat | 540 |
| agaaaactaa | gtgagtcctg | accaatttat | caaccaattg | atgggaccaa | gcagggcaaa | 600 |
| ggaaggata | gtagtgggtg | gagttcaact | gaagcaacaa | cggcaaaaaa | tgatgcgccc | 660 |
| agtgtttctg | gagggagatc | atcagacaac | gcttcaaaat | tcaccaagta | cctcaacacc | 720 |
| aaacaagcgt | tagagagcat | cggtatcttg | tttgatgatc | aaaccccaag | aaatgttatc | 780 |
| acccaactct | attatgcttc | tactagcaag | ctagcagtca | ccaacaacca | cattgtcgtg | 840 |
| atgggtaaca | gctttctacc | cagcatgtgg | tactgggtgg | tggagcggag | tgcaacaact | 900 |
| gattcatcat | caaaacccac | ctggtttgct | aataccaatt | tagactgagg | ggaagacaaa | 960 |
| caaaaacaat | ttgttgagaa | ccagttgggg | tataaggaaa | ctaccagtac | caattcccac | 1020 |
| aacttccatt | ccaaatcttt | cacccaactt | gcatatctga | tcagtggcat | tgacagtgtc | 1080 |

```
aatgatcaaa tcatcttcag tggctttaaa gcggggagtg tggggtatga tagtagtagt    1140
agtagtagta gtagtagtag tagtagtagt agtaccaaag accaagcact tgcttgatca    1200
acaacaacta gcttagatag taaaacgggg tataaggatt tggtgaccaa cgacacggga    1260
ttaaatggtc cgatcaatgg gagttttttca atccaagaca ccttctcatt cgttgttcct    1320
tattcgggga atcatacaaa taatggaaca actggaccca ttaaaactgc ttatccagtg    1380
aaaaaagatc aaaaatcaac tgtcaagatc aattctttga ttaacgctac gcccttgaat    1440
agttatgggg atgagtgggat tggggtgttt gatgcgttag gtt                     1483
```

<210> SEQ ID NO 25
<211> LENGTH: 657
<212> TYPE: DNA
<213> ORGANISM: Unknown
<220> FEATURE:
<223> OTHER INFORMATION: Multiple organisms which demonstrate resistance to penicillin group antimicrobials

<400> SEQUENCE: 25

```
atggatatta ttgataaagt ttttcagcaa gaggatttct cacgccagga tttgagtgac     60
agccgttttc gccgctgccg ctttttatcag tgtgacttca gccactgtca gctgcaggat    120
gccagtttcg aggattgcag tttcattgaa agcggcgccg ttgaagggtg tcacttcagc    180
tatgccgatc tgcgcgatgc cagtttcaag gcctgccgtc tgtctttggc caacttcagc    240
ggtgccaact gctttggcat agagttcagg gagtgcgatc tcaagggcgc caacttttcc    300
cgggcccgct tctacaatca agtcagccat aagatgtact tctgctcggc ttatatctca    360
ggttgcaacc tggcctatac caacttgagt ggccaatgcc tggaaaaatg cgagctgttt    420
gaaaacaact ggagcaatgc caatctcagc ggcgcttcct tgatgggctc agatctcagc    480 cgcggcaccct tctcccgcga ctgttggcaa caggtcaatc tgcggggctg tgacctgacc    540
tttgccgatc tggatgggct cgaccccaga cgggtcaacc tcgaaggagt caagatctgt    600
gcctggcaac aggagcaact gctggaaccc ttgggagtaa tagtgctgcc ggattag       657
```

<210> SEQ ID NO 26
<211> LENGTH: 861
<212> TYPE: DNA
<213> ORGANISM: Unknown
<220> FEATURE:
<223> OTHER INFORMATION: Multiple organisms which demonstrate resistance to penicillin group antimicrobials

<400> SEQUENCE: 26

```
atgagtattc aacatttttcg tgtcgccctt attcccttttt ttgcggcatt ttgccttcct    60 gttttttgctc acccagaaac gctggtgaaa gtaaaagatg ctgaagatca gttgggtgca    120
cgagtgggtt acatcgaact ggatctcaac agcggtaaga tccttgagag ttttcgcccc    180
gaagaacgtt ttccaatgat gagcactttt aaagttctgc tatgtggtgc ggtattatcc    240
cgtgttgacg ccgggcaaga gcaactcggt cgccgcatac actattctca gaatgacttg    300
gttgagtact caccagtcac agaaaagcat cttacggatg gcatgacagt aagagaatta    360
tgcagtgctg ccataaccat gagtgataac actgctgcca acttacttct gacaacgatc    420
ggaggaccga aggagctaac cgcttttttg cacaacatgg gggatcatgt aactcgcctt    480
gatcgttggg aaccggagct gaatgaagcc ataccaaacg acgagcgtga ccacacgatg    540
cctgcagcaa tggcaacaac gttgcgcaaa ctattaactg gcgaactact tactctagct    600
```

```
tcccggcaac aattaataga ctggatggag gcggataaag ttgcaggacc acttctgcgc    660
tcggcccttc cggctggctg gtttattgct gataaatctg gagccggtga gcgtgggtct    720
cgcggtatca ttgcagcact ggggccagat ggtaagccct cccgtatcgt agttatctac    780
acgacgggga gtcaggcaac tatggatgaa cgaaatagac agatcgctga gataggtgcc    840
tcactgatta agcattggta a                                              861
```

<210> SEQ ID NO 27
<211> LENGTH: 478
<212> TYPE: DNA
<213> ORGANISM: Unknown
<220> FEATURE:
<223> OTHER INFORMATION: Multiple organisms which demonstrate resistance
to ciproflaxin antimicrobials

<400> SEQUENCE: 27

```
aggtggctca gtatgggca tcattcgcac atgtaggctc ggccctgacc aagtcaaatc     60
catgagggct gctcttgatc ttttcggtcg tgagttcgga gacgtagcca cctactccca   120
acatcagccg gactccgatt acctcgggaa cttgctccgt agtaagacat tcatcgcgct   180
tgctgccttc gaccaagaag cggttgttgg cgctctcgcg gcttacgttc tgccaaagtt   240
tgagcaggcg cgtagtgaga tctatatcta tgatctcgca gtctccggcg agcaccggag   300
gcaaggcatt gccaccgcgc tcatcaatct cctcaagcat gaggccaacg cgcttggtgc   360
ttatgtgatc tacgtgcaag cagattacgg tgacgatccc gcagtggctc tctatacaaa   420
gttgggcata cgggaagaag tgatgcactt tgatatcgac ccaagtaccg ccacctaa     478
```

<210> SEQ ID NO 28
<211> LENGTH: 657
<212> TYPE: DNA
<213> ORGANISM: Unknown
<220> FEATURE:
<223> OTHER INFORMATION: Multiple organisms which demonstrate resistance
to ciproflaxin antimicrobials

<400> SEQUENCE: 28

```
atggatatta ttgataaagt ttttcagcaa gaggatttct cacgccagga tttgagtgac     60
agccgttttc gccgctgccg cttttatcag tgtgacttca gccactgtca gctgcaggat   120
gccagtttcg aggattgcag tttcattgaa agcggcgccg ttgaagggtg tcacttcagc   180
tatgccgatc tgcgcgatgc cagtttcaag gcctgccgtc tgtctttggc caacttcagc   240
ggtgccaact gctttggcat agagttcagg gagtgcgatc tcaagggcgc caactttttcc   300 cgggcccgct tctacaatca agtcagccat aagatgtact tctgctcggc ttatatctca   360
ggttgcaacc tggcctatac caacttgagt ggccaatgcc tggaaaaatg cgagctgttt   420
gaaaacaact ggagcaatgc caatctcagc ggcgcttcct tgatgggctc agatctcagc   480
cgcggcacct tctcccgcga ctgttggcaa caggtcaatc tgcggggctg tgacctgacc   540
tttgccgatc tggatgggct cgaccccaga cgggtcaacc tcgaaggagt caagatctgt   600
gcctggcaac aggagcaact gctggaaccc ttgggagtaa tagtgctgcc ggattag       657
```

<210> SEQ ID NO 29
<211> LENGTH: 681
<212> TYPE: DNA
<213> ORGANISM: Unknown
<220> FEATURE:
<223> OTHER INFORMATION: Multiple organisms which demonstrate resistance
to levoflaxacin antimicrobials

<400> SEQUENCE: 29

```
atgacgccat tactgtataa aaaaacaggt acaaatatgg ctctggcact cgttggcgaa    60
aaaattgaca gaaaccgttt caccggtgag aaaattgaaa atagtacatt ttttaactgt   120
gatttttcag gtgccgacct gagcggcact gaatttatcg gctgtcagtt ctatgatcgt   180
gaaagccaga aagggtgcaa ttttagtcgt gcgatgctga agatgccat ttttaaaagc    240
tgtgatttat ccatggcgga ttttcgcaat gccagtgcgc tgggcattga aattcgccac   300
tgccgcgcac aaggcgcaga tttccgcggc gcaagcttta tgaatatgat caccacgcgc   360
acctggtttt gtagcgcata tatcacgaat accaatctaa gctacgccaa ttttcgaaa    420
gtcgtgttgg aaaagtgtga gctgtgggaa accgttgga tgggtgccca ggtactgggc    480
gcgacgttca gtggttcaga tctctccggc ggcgagtttt cgactttcga ctggcgagca   540
gcgaacttca cacattgcga tctgaccaat tcggagttgg gtgacttaga tattcggggc   600
gttgatttac aaggcgttaa gctggacaac taccaggcgt cgttgctcat ggagcggctt   660
ggcatcgcgg tgattggtta g                                             681
```

<210> SEQ ID NO 30
<211> LENGTH: 600
<212> TYPE: DNA
<213> ORGANISM: Unknown
<220> FEATURE:
<223> OTHER INFORMATION: Multiple organisms which demonstrate resistance to levoflaxacin antimicrobials

<400> SEQUENCE: 30

```
atgagcaacg caaaaacaaa gttaggcatc acaaagtaca gcatcgtgac caactgcaac    60
gattccgtca cactgcgcct catgactgag catgaccttg cgatgctcta tgggtggcta   120
aatcgatctc atatcgtcga gtggtggggc ggagaagaag cacgcccgac acttgctgac   180
gtacaggaac agtacttgcc aagcgtttta gcgcaagagt ccgtcactcc atacattgca   240
atgctgaatg gagagccgat tgggtatgcc cagtcgtacg ttgctcttgg aagcggggac   300
ggacggtggg aagaagaaac cgatccagga gtacgcggaa tagaccagtt actggcgaat   360
gcatcacaac tgggcaaagg cttgggaacc aagctggttc gagctctggt tgagttgctg   420
ttcaatgatc ccgaggtcac caagatccaa acggacccgt cgccgagcaa cttgcgagcg   480
atccgatgct acgagaaagc gggtttgag aggcaaggta ccgtaaccac cccatatggt    540
ccagccgtgt acatggttca aacacgccag gcattcgagc gaacacgcag tgatgcctaa   600
```

<210> SEQ ID NO 31
<211> LENGTH: 1161
<212> TYPE: DNA
<213> ORGANISM: Unknown
<220> FEATURE:
<223> OTHER INFORMATION: Multiple organisms which demonstrate resistance to cephalexin antimicrobials

<400> SEQUENCE: 31

```
atgcagaaca cattgaagct gttatccgtg attacctgtc tggcagcaac tgtccaaggt    60
gctctggctg ctaatatcga tgagagcaaa attaaagaca ccgttgatga cctgatccag   120
ccgctgatgc agaagaataa tattcccggt atgtcggtcg cagtgaccgt caacggtaaa   180
aactacattt ataactatgg gttagcggca aaacagcctc agcagccggt tacggaaaat   240
acgttatttg aagtgggttc gctgagtaaa acgtttctg ccaccttggc gtcctatgcg    300
caggtgagcg gtaagctgtc tttggatcaa agcgttagcc attacgttcc agagttgcgt   360
```

```
ggcagcagct ttgaccacgt tagcgtactc aatgtgggca cgcatacctc aggcctacag    420
ctatttatgc cggaagatat taaaaatacc acacagctga tggcttatct aaaagcatgg    480
aaacctgccg atgcggctgg aacccatcgc gtttattcca atatcggtac tggtttgcta    540
gggatgattg cggcgaaaag tctgggtgtg agctatgaag atgcgattga gaaaaccctc    600
cttcctcagt taggcatgca tcacagctac ttgaaggttc cggctgacca gatggaaaac    660
tatgcgtggg gctacaacaa gaaagatgag ccagtgcacg ggaatatgga gattttgggt    720
aacgaagctt atggtatcaa aaccacctcc agcgacttgt tacgctacgt gcaagccaat    780
atggggcagt taaagcttga tgctaatgcc aagatgcaac aggctctgac agccaccccac  840 accggctatt tcaaatcggg tgagattact caggatctga tgtgggagca gctgccatat   900
ccggtttctc tgccgaattt gctcaccggt aacgatatgg cgatgacgaa aagcgtggct   960
acgccgattg ttccgccgtt accgccacag gaaaatgtgt ggattaataa gaccggatca  1020
actaacggct tcggtgccta tattgcgttt gttcctgcta agaagatggg gatcgtgatg  1080
ctggctaaca aaaactactc aatcgatcag cgagtgacgg tggcgtataa aatcctgagc  1140
tcattggaag ggaataagta g                                            1161
```

<210> SEQ ID NO 32
<211> LENGTH: 1364
<212> TYPE: DNA
<213> ORGANISM: Unknown
<220> FEATURE:
<223> OTHER INFORMATION: Multiple organisms which demonstrate resistance
      to cephalexin antimicrobials

<400> SEQUENCE: 32

```
atagtgattt ttgaagctaa taaaaaacac acgtggaatt taggaaaaac ttatatctgc     60
tgctaaattt aaccgtttgt caacacggtg caaatcaaac acactgattg cgtctgacgg    120
gcccggacac cttttttgctt ttaattacgg aactgatttc atgatgaaaa aatcgttatg    180
ctgcgctctg ctgctgacag cctctttctc cacatttgct gccgcaaaaa cagaacaaca    240
gattgccgat atcgttaatc gcaccatcac cccgttgatg caggagcagg ctattccggg    300 tatgccgtt gccgttatct accagggaaa accctattat ttcacctggg gtaaagccga    360
tatcgccaat aaccacccag tcacgcagca aacgctgttt gagctaggat cggttagtaa    420
gacgtttaac ggcgtgttgg gcggcgatgc tatcgcccgc ggcgaaatta agctcagcga    480
tccggtcacg aaatactggc cagaactgac aggcaaacag tggcagggta tccgcctgct    540
gcacttagcc acctatacgg caggcggcct accgctgcag atccccgatg acgttaggga    600
taaagccgca ttactgcatt tttatcaaaa ctggcagccg caatggactc cgggcgctaa    660
gcgactttac gctaactcca gcattggtct gtttggcgcg ctggcggtga aaccctcagg    720
aatgagttac gaagaggcaa tgaccagacg cgtcctgcaa ccattaaaac tggcgcatac    780
ctggattacg gttccgcaga acgaacaaaa agattatgcc tggggctatc gcgaagggaa    840
gcccgtacac gtttctccgg gacaacttga cgccggagcc tatggcgtga atccagcgt    900 tattgatatg gcccgctggg ttcaggccaa catggatgcc agccacgttc aggagaaaac    960
gctccagcag ggcattgcgc ttgcgcagtc tcgctactgg cgtattggcg atatgtacca  1020
gggattaggc tgggagatgc tgaactggcc gctgaaagct gattcgatca tcaacggcag  1080
cgacagcaaa gtggcattgg cagcgcttcc cgccgttgag gtaaacccgc ccgccccgc   1140 agtgaaagcc tcatgggtgc ataaaacggg ctccactggt ggatttggca gctacgtagc  1200
```

```
cttcgttcca gaaaaaaacc ttggcatcgt gatgctggca aacaaaagct atcctaaccc    1260
tgtccgtgtc gaggcggcct ggcgcattct tgaaaagctg caataactga cgatgaggcc    1320
caggatattg ggcctccttt ctttctcttt ttttcctgtg tcat                     1364
```